United States Patent [19]
Ames et al.

[11] Patent Number: 5,942,405
[45] Date of Patent: Aug. 24, 1999

[54] THERAPEUTIC AND SCREENING METHODS USING C3A RECEPTOR AND C3A

[75] Inventors: Robert S Ames, Havertown; Derk Jon Bergsma, Berwyn; James J Foley, Radnor, all of Pa.; Chandrika Saidapet-Kumar, West Windsor, N.J.; Henry M Sarau, Harleysville, Pa.

[73] Assignee: SmithKline Beecham Corporation, Philadelphia, Pa.

[21] Appl. No.: 08/876,874

[22] Filed: Jun. 16, 1997

Related U.S. Application Data

[60] Provisional application No. 60/019,627, Jun. 17, 1996.
[51] Int. Cl.$^6$ .......................... G01N 33/566; G01N 33/58
[52] U.S. Cl. ........................ 435/7.24; 435/7.21; 436/501; 436/821
[58] Field of Search ................................. 435/7.21, 7.24; 436/821, 501

[56] References Cited

U.S. PATENT DOCUMENTS 5,861,272  1/1999  Li ........................................... 435/69.1

FOREIGN PATENT DOCUMENTS

| WO96/25432 | 8/1996 | European Pat. Off. . |
|---|---|---|
| 814158 | 12/1997 | European Pat. Off. . |
| WO 96/39511 | 12/1996 | WIPO . |

OTHER PUBLICATIONS

Crass, T., et al., "Expression cloning of the human C3a anaphylatoxin receptor (C3aR) from differentiated U–937 cells", *Eur. J. Immunol.*, 26: 1944–1950, (1996).

Roglic, A., et al., "cDNA cloning of a novel G protein-coupled receptor with a large extracellular loop structure", *Biochimica et Biophysica Acta*, 1305: 39–43 (1996).

Ames, Robert S., et al., "Molecular cloning and characterization of the human anaphylatoxin C3a receptor", *J. Biolog. Chem.*, 271(34): 20231–20234 (1996).

*Primary Examiner*—David Saunders
*Assistant Examiner*—Mary Beth Tung
*Attorney, Agent, or Firm*—William T. Han; William T. King; Charles M. Kinzig

[57] ABSTRACT

Human C3a Receptor polypeptides and DNA (RNA) encoding such C3a Receptor and a procedure for producing such polypeptides by recombinant techniques is disclosed. Also disclosed are methods for utilizing such C3a Receptor for the treatment of inflammatory and auto-immune disorders, among others. Antagonists against such C3a Receptor and their use as a therapeutic to treat inflammatory and auto-immune disorders, among others, are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding the C3a Receptor and for detecting altered levels of the polypeptide in a host.

8 Claims, 12 Drawing Sheets

```
-152  CACGAGGAGAACAGAGAAGAGAAAGCTCAGCAAATTTCTTGCCATATACTTCATGACTTC  -93
 -92  ACTGTGGCTAAGTGTGGGGACCAGACATCGTGGAGACATCCAGTGCTGAAGCCTT       -33
 -32  CAGCTACTGTCTCAGTTTTTTGAAGTTTAGCAATGGCGTCTTTCTGCTGAGACCAATT     28
                                    M  A  S  F  S  A  E  T  N  S
  29  CAACTGACCTACTCTCACAGCCCCAGTAATTCTCTCCATGGTCATTC                88
       T  D  L  L  S  Q  P  W  N  E  P  P  V  I  L  S  M  V  I  L
  89  TCAGCCTTACTTTTTACTGGGATTGCCAGGCAATGGGCTGTGGTGGCTGGCC          148
       S  L  T  F  L  L  G  L  P  G  N  G  L  V  L  W  V  A  G  L
 149  TGAAGATGCAGCGGACAGTGAACACAATTGGTTCCTCCACCTGGCGGACCTCC         208
       K  M  Q  R  T  V  N  T  I  W  F  L  H  L  T  L  A  D  L  L
 209  TCTGCTGCCTCTCCTTGCCCTTCTCGCTGGTCACTTGGCTCTCCAGGACAGTGGCCCT    268
       C  C  L  S  L  P  F  S  L  A  H  L  A  L  Q  G  Q  W  P  Y
 269  ACGGCAGGTTCCTATGCCAAGCTCATCCCCATCATTGTCCTCAACATGTTGCCAGTG     328
       G  R  F  L  C  K  L  I  P  S  I  H  V  L  N  M  F  A  S  V
 329  TCTTCCTGCTTACTGCCATTAGCCCTGGATCGCTGTCTTGTGGTATTCAAGCCAATCTGT 388
       F  L  T  A  I  S  L  D  R  C  L  V  V  F  K  P  I  W  C
 389  GTCAGAATCATCGCAATGTAGGGATGGCCTGCTCTATCTGTGATGTATCTGGGTGGTGG  448
       Q  N  H  R  N  V  G  M  A  C  S  I  C  G  C  I  W  V  V  A
 449  CTTGTGTGATGTGCATTCCTGTGTTCGTGTACCGGGAAATCTTCACTACAGACAACCATA 508
       C  V  M  C  I  P  V  F  V  Y  R  E  I  F  T  T  D  N  H  N
```

FIG. 1A-1

```
 509  ATAGATGTGGCTACAAATTGGTCTCTCCAGCTCATTAGATTATCCAGACTTTTATGGAG   568
        R  C  G  Y  K  F  G  L  S  S  L  D  Y  P  D  F  Y  G  D
 569  ATCCACTAGAAACAGTCTCTTGAAAACATTGTTCAGCCGCCTGGAGAAATGAATGATA   628
        P  L  E  N  R  S  L  E  N  I  V  Q  P  P  G  E  M  N  D  R
 629  GGTTAGATCCTCCTCTCTTCCAAACAAATGATCATCCTTGGACAGTCCCCACTGTCTTCC   688
         L  D  P  S  S  F  Q  T  N  D  H  P  W  T  V  P  T  V  F  Q
 689  AACCTCAAACATTCAAAGACCTTCTGCAGATTCACTCCCTAGGGGTTCTGCTAGGTTAA   748
        P  Q  T  F  Q  R  P  S  A  D  S  L  P  R  G  S  A  R  L
 749  CAAGTCAAAATCTGTATTCTAATGTATTTAAACCTGCTGATGTGGTCTCACCTAAAATCC   808
        S  Q  N  L  Y  S  N  V  F  K  P  A  D  V  S  P  K  I  P
 809  CCAGTGGGTTTCCTATTGAAGATCACGAAACCAGCCCACTGGATAACTCTGATGCTTTTC   868
        S  G  F  P  I  E  D  H  E  T  S  P  L  D  N  S  D  A  F  L
 869  TCTCTACTCATTTAAAGCTTTCCTAGCGTTCCTAGCCTTCTAGCAATTCCTTCTACGAGTCTGAGC   928
         S  T  H  L  K  L  F  P  S  A  S  S  N  S  F  Y  E  S  E  L
 929  TACCACAAGGTTTCCAGGATTATTACAATTAGGCCAATTCACAGATGACGATCAAGTGC   988
        P  Q  G  F  Q  D  Y  Y  N  L  G  Q  F  T  D  D  D  Q  V  P
 989  CAACACCCCTCGTGGCAATAACGATCACTAGGCTAGTGGGTTTCCTGCTCCCTCTG   1048
        T  P  L  V  A  I  T  I  T  R  L  V  V  G  F  L  L  P  S  V
1049  TTATCATGATAGCCTGTTACAGCTTCATTGTCTTCCGAATGCAAAGGGGCCGCTTCGCCA   1108
        I  M  I  A  C  Y  S  F  I  V  F  R  M  Q  R  G  R  F  A  K
```

FIG. 1A-2

```
1109  AGTCTCAGAGCAAAACCTTTCGAGTGGCCGTGGTGGTGGCCGTGTTCTTTGTCTGCT  1168
       S   Q   S   K   T   F   R   V   A   V   V   V   A   V   F   L   V   C   W
1169  GGACTCCATACCACATTTTTGGAGTCCTGTCATTGCTTACTGACCCAGAAACTCCCTTGG  1228
       T   P   Y   H   I   F   G   V   L   S   L   L   T   D   P   E   T   P   L   G
1229  GGAAAACTCTGATGTCCTGGGATCATGTATGCATTCCTAGCATCTGCCAATAGTTGCT  1288
       K   T   L   M   S   W   D   H   V   C   I   A   L   A   S   A   N   S   C   F
1289  TTAATCCCTTCCTTTATGCCCTCTTGGGGAAAGATTTTAGGAAAGCAAGGCAGTCCA  1348
       N   P   F   L   Y   A   L   L   G   K   D   F   R   K   K   A   R   Q   S   I
1349  TTCAGGGAATTCTGGAGGCAGCCTTCAGTGAGGAGCTCACACGTTCCACCCACTGTCCT  1408
       Q   G   I   L   E   A   A   F   S   E   E   L   T   R   S   T   H   C   P   S
1409  CAAACAATGTCATTTCAGAAAGAATAGTACAACTGTGTGAAAATGTGGAGCAGCCAACA  1468
       Q   N   V   I   S   E   R   N   S   T   T   V   *
1469  AGCAGGGGCTCTTAGGCAATCACATAGTGAAAGTTTATAAGAGGATGAAGTGATATGGTG  1528
1529  AGCAGCGGACTTCAAAAACTGTCAAAGAATCAATCCAGCGGTTCTCAAACGTACACAGA  1588
1589  CTATTGACATCAGCATCACCTAGAAATCGTTAGAAATGCAAATTCTCAAGCCGCATCCC  1648
1649  AGACTTGCTGAATCGGAATCTCTGGGGGTTGGGACCCAGCAAGGCACTTAACAAACCCC  1708
1709  CGTTTCTGATTAATGCTAAATGTAAGAATCATTGTAAACATTAGTTCTATTCTATCCA  1768
1769  AACTAAGCTATGTGAAATAAGAGAAGCTACTTTGTTTTTAAATGATGTTGAATATTGTC  1828
1829  GATATTTCCATCATTAAATTTTTCCTTAGCATTGTCTAAGTGTCAAAAAAAAAAAAAAA  1888
```

FIG. 1A-3

```
  1 MASFSAETNSTDLLSQP....WNEP............PVILSMVILSLTFLL  36
    |·||·|·  ·:·   :·|·|          :|·|     |||·:||·:||·:
  1 MNSFNYTTPDYGHYDDKDTLDLNTPVDKTSNTLRVPDILALVIFAVVFLV    50

37 GLPGNGLVLWVAGLKMQRTVNTIWFLHLTLADLLCCLSLPFSLAHLALQG    86
    |·||·||·|·  ·::·  ·||·|·||||·::·||·||·||·  · :· ::
 51 GVLGNALVVWVTAFEAKRTINAIWFLNLAVADFLSCLALPILFTSIVQHH   100

87 QWPYGRFLCKLIPSIIVLNMFASVFLLTAISLDRCLVVFKPIWCQNHRNV   136
    :·||·|   |·|·||·:||·||||·::·||·||·||||||||||·|··|
101 HWPFGGAACSILPSLILLNMYASILLLATISADRFLLVFKPIWCQNFRGA   150

137 GMACSICGCIWVVACVMCIPVFVYREIFTTDNHNRCGYKFGLSSSLDYPD   186
    |·:|    |·|·|·:·||·:|·||·|||·:|
151 GLAWIACAVAWGLALLLTIPSFLYRVV......................   177

237 PSADSLPRGSARLTSQNLYSNVFKPADVVSPKIPSGFPIEDHETSPLDNS   286
                       ·:··:||·:|
178 .............................REEYFPPKVLCG.......   189
```

FIG. 2A

287 DAFLSTHLKLFPSASSNSFYESELPQGFQDYNLGQFTDDDQVPTPLVAI 336
                                  ::|:. .|:
190 ..................................VDYSHDKR...RERAV 202

337 TITRLVVGFLLPSVIMIACYSFIVFRMQRGRFAKSQSKTFRVAVVVAVF 386
    .|.||||:||:| :||.|| ::.||... .||:|.|.:|||
203 AIVRLVLGFLWPLLTLTICYTFILLRT.WSRRATRSTKTLKVVVAVVASF 251

387 LVCWTPYHIFGVLSLLTDPETPLGKTLMSWDHVCIALASANSCFNPFLYA 436
    :: | ||| |:: : :|::. .:| |:||:| |:|::|.
252 FIFWLPYQVTGIMMSFLEPSSPTFLLNKLDSLCVSFAYINCCINPIIYV 301

437 LLGKDFRKKARQSIQGILEAAFSEE.LTRSTHCPSNNVISERNSTT 481
    .|.:.|:|.:|.:| ...::.|.:.
302 VAGQFQGRLRKSLPSLLRNVLTEESVVRESKSFTRSTVDTMAQKT 347

FIG. 2B

```
   1  ATGGCGTCTT TCTCTGCTGA GACCAATTCA ACTGACCTAC TCTCACAGCC
  51  ATGGAATGAG CCCCCAGTAA TTCTCTCCAT GGTCATTCTC AGCCTTACTT
 101  TTTTACTGGG ATTGCCAGGC AATGGGCTGG TGCTGTGGGT GGCTGGCCTG
 151  AAGATGCAGC GGACAGTGAA CACAATTTGG TTCCTCCACC TCACCTTGGC
 201  GGACCTCCTC TGCTGCCTCT CCTTGCCCTT CTCGCTGGCT CACTTGGCTC
 251  TCCAGGGACA GTGGCCCTAC GGCAGGTTCC TATGCAAGCT CATCCCCTCC
 301  ATCATTGTCC TCAACATGTT TGCCAGTGTC TTCCTGCTTA CTGCCATTAG
 351  CCTGGATCGC TGTCTTGTGG TATTCAAGCC AATCTGGTGT CAGAATCATC
 401  GCAATGTAGG GATGGCCTGC TCTATCTGTG GATGTATCTG GGTGGTGGCT
 451  TTTGTGATGT GCATTCCTGT GTTCGTGTAC CGGGAAATCT TCACTACAGA
 501  CAACCATAAT AGATGTGGCT ACAAATTTGG TCTCTCCAGC TCATTAGATT
 551  ATCCAGACTT TTATGGAGAT CCACTAGAAA ACAGGTCTCT TGAAAACATT
 601  GTTCAGCCGC CTGGAGAAAT GAATGATAGG TTAGATCCTT CCTCTTTCCA
 651  AACAAATGAT CATCCTTGGA CAGTCCCCAC TGTCTTCCAA CCTCAAACAT
 701  TTCAAAGACC TTCTGCAGAT TCACTCCCTA GGGGTTCTGC TAGGTTAACA
 751  AGTCAAAATC TGTATTCTAA TGTATTTAAA CCTGCTGATG TGGTCTCACC
 801  TAAAATCCCC AGTGGGTTTC CTATTGAAGA TCACGAAACC AGCCCACTGG
 851  ATAACTCTGA TGCTTTTCTC TCTACTCATT TAAAGCTGTT CCCTAGCGCT
 901  TCTAGCAATT CCTTCTACGA GTCTGAGCTA CCACAAGGTT CCAGGATTA
 951  TTACAATTTA GGCCAATTCA CAGATGACGA TCAAGTGCCA ACACCCCTCG
1001  TGGCAATAAC GATCACTAGG CTAGTGGTGG GTTTCCTGCT GCCCTCTGTT
1051  ATCATGATAG CCTGTTACAG CTTCATTGTC TTCCGAATGC AAAGGGGCCG
1101  CTTCGCCAAG TCTCAGAGCA AAACCTTTCG AGTGGCCGTG GTGGTGGTGG
1151  CTGTCTTTCT TGTCTGCTGG ACTCCATACC ACATTTTTGG AGTCCTGTCA
1201  TTGCTTACTG ACCCAGAAAC TCCCTTGGGG AAAACTCTGA TGTCCTGGGA
1251  TCATGTATGC ATTGCTCTAG CATCTGCCAA TAGTTGCTTT AATCCCTTCC
1301  TTTATGCCCT CTTGGGGAAA GATTTTAGGA AGAAAGCAAG GCAGTCCATT
1351  CAGGGAATTC TGGAGGCAGC CTTCAGTGAG GAGCTCACAC GTTCCACCCA
1401  CTGTCCCTCA AACAATGTCA TTTCAGAAAG AAATAGTACA ACTGTGTGA
```

FIG. 6

1    MASFSAETNS TDLLSQPWNE PPVILSMVIL SLTFLLGLPG NGLVLWVAGL
51   KMQRTVNTIW FLHLTLADLL CCLSLPFSLA HLALQGQWPY GRFLCKLIPS
101  IIVLNMFASV FLLTAISLDR CLVVFKPIWC QNHRNVGMAC SICGCIWVVA
151  CVMCIPVFVY REIFTTDNHN RCGYKFGLSS SLDYPDFYGD PLENRSLENI
201  VQPPGEMNDR LDPSSFQTND HPWTVPTVFQ PQTFQRPSAD SLPRGSARLT
251  SQNLYSNVFK PADVVSPKIP SGFPIEDHET SPLDNSDAFL STHLKLFPSA
301  SSNSFYESEL PQGFQDYYNL GQFTDDDQVP TPLVAITITR LVVGFLLPSV
351  IMIACYSFIV FRMQRGRFAK SQSKTFRVAV VVVAVFLVCW TPYHIFGVLS
401  LLTDPETPLG KTLMSWDHVC IALASANSCF NPFLYALLGK DFRKKARQSI
451  QGILEAAFSE ELTRSTHCPS NNVISERNST TV*

FIG. 7

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 1449 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
ATGGCGTCTT TCTCTGCTGA GACCAATTCA ACTGACCTAC TCTCACAGCC ATGGAATGAG      60
CCCCCAGTAA TTCTCTCCAT GGTCATTCTC AGCCTTACTT TTTTACTGGG ATTGCCAGGC     120
AATGGGCTGG TGCTGTGGGT GGCTGGCCTG AAGATGCAGC GGACAGTGAA CACAATTTGG     180
TTCCTCCACC TCACCTTGGC GGACCTCCTC TGCTGCCTCT CCTTGCCCTT CTCGCTGGCT     240
CACTTGGCTC TCCAGGGACA GTGGCCCTAC GGCAGGTTCC TATGCAAGCT CATCCCCTCC     300
ATCATTGTCC TCAACATGTT TGCCAGTGTC TTCCTGCTTA CTGCCATTAG CCTGGATCGC     360
TGTCTTGTGG TATTCAAGCC AATCTGGTGT CAGAATCATC GCAATGTAGG GATGGCCTGC     420
TCTATCTGTG GATGTATCTG GGTGGTGGCT TTTGTGATGT GCATTCCTGT GTTCGTGTAC     480
CGGGAAATCT TCACTACAGA CAACCATAAT AGATGTGGCT ACAAATTTGG TCTCTCCAGC     540
TCATTAGATT ATCCAGACTT TTATGGAGAT CCACTAGAAA CAGGTCTCT TGAAAACATT      600
GTTCAGCCGC CTGGAGAAAT GAATGATAGG TTAGATCCTT CCTCTTTCCA AACAAATGAT     660
CATCCTTGGA CAGTCCCCAC TGTCTTCCAA CCTCAAACAT TCAAAGACC TTCTGCAGAT      720
TCACTCCCTA GGGGTTCTGC TAGGTTAACA AGTCAAAATC TGTATTCTAA TGTATTTAAA     780
CCTGCTGATG TGGTCTCACC TAAAATCCCC AGTGGGTTTC CTATTGAAGA TCACGAAACC     840
AGCCCACTGG ATAACTCTGA TGCTTTTCTC TCTACTCATT TAAAGCTGTT CCCTAGCGCT     900
TCTAGCAATT CCTTCTACGA GTCTGAGCTA CCACAAGGTT TCCAGGATTA TTACAATTTA     960
GGCCAATTCA CAGATGACGA TCAAGTGCCA ACACCCCTCG TGGCAATAAC GATCACTAGG    1020
CTAGTGGTGG GTTTCCTGCT GCCCTCTGTT ATCATGATAG CCTGTTACAG CTTCATTGTC    1080
TTCCGAATGC AAAGGGGCCG CTTCGCCAAG TCTCAGAGCA AAACCTTTCG AGTGGCCGTG    1140
GTGGTGGTGG CTGTCTTTCT TGTCTGCTGG ACTCCATACC ACATTTTTGG AGTCCTGTCA    1200
TTGCTTACTG ACCCAGAAAC TCCCTTGGGG AAAACTCTGA TGTCCTGGGA TCATGTATGC    1260
ATTGCTCTAG CATCTGCCAA TAGTTGCTTT AATCCCTTCC TTTATGCCCT CTTGGGGAAA    1320
GATTTTAGGA AGAAAGCAAG GCAGTCCATT CAGGGAATTC TGGAGGCAGC CTTCAGTGAG    1380
GAGCTCACAC GTTCCACCCA CTGTCCCTCA AACAATGTCA TTTCAGAAAG AAATAGTACA    1440
ACTGTGTGA                                                           1449
```

(2) INFORMATION FOR SEQ ID NO:2:

(i) SEQUENCE CHARACTERISTICS:
        (A) LENGTH: 482 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ala Ser Phe Ser Ala Glu Thr Asn Ser Thr Asp Leu Leu Ser Gln
 1               5                  10                  15
```

-continued

```
Pro Trp Asn Glu Pro Pro Val Ile Leu Ser Met Val Ile Leu Ser Leu
             20                  25                  30

Thr Phe Leu Leu Gly Leu Pro Gly Asn Gly Leu Val Leu Trp Val Ala
         35                  40                  45

Gly Leu Lys Met Gln Arg Thr Val Asn Thr Ile Trp Phe Leu His Leu
     50                  55                  60

Thr Leu Ala Asp Leu Leu Cys Cys Leu Ser Leu Pro Phe Ser Leu Ala
65                   70                  75                  80

His Leu Ala Leu Gln Gly Gln Trp Pro Tyr Gly Arg Phe Leu Cys Lys
                 85                  90                  95

Leu Ile Pro Ser Ile Ile Val Leu Asn Met Phe Ala Ser Val Phe Leu
             100                 105                 110

Leu Thr Ala Ile Ser Leu Asp Arg Cys Leu Val Val Phe Lys Pro Ile
         115                 120                 125

Trp Cys Gln Asn His Arg Asn Val Gly Met Ala Cys Ser Ile Cys Gly
     130                 135                 140

Cys Ile Trp Val Val Ala Cys Val Met Cys Ile Pro Val Phe Val Tyr
145                 150                 155                 160

Arg Glu Ile Phe Thr Thr Asp Asn His Asn Arg Cys Gly Tyr Lys Phe
                 165                 170                 175

Gly Leu Ser Ser Ser Leu Asp Tyr Pro Asp Phe Tyr Gly Asp Pro Leu
             180                 185                 190

Glu Asn Arg Ser Leu Glu Asn Ile Val Gln Pro Pro Gly Glu Met Asn
         195                 200                 205

Asp Arg Leu Asp Pro Ser Ser Phe Gln Thr Asn Asp His Pro Trp Thr
     210                 215                 220

Val Pro Thr Val Phe Gln Pro Gln Thr Phe Gln Arg Pro Ser Ala Asp
225                 230                 235                 240

Ser Leu Pro Arg Gly Ser Ala Arg Leu Thr Ser Gln Asn Leu Tyr Ser
                 245                 250                 255

Asn Val Phe Lys Pro Ala Asp Val Val Ser Pro Lys Ile Pro Ser Gly
             260                 265                 270

Phe Pro Ile Glu Asp His Glu Thr Ser Pro Leu Asp Asn Ser Asp Ala
         275                 280                 285

Phe Leu Ser Thr His Leu Lys Leu Phe Pro Ser Ala Ser Ser Asn Ser
     290                 295                 300

Phe Tyr Glu Ser Glu Leu Pro Gln Gly Phe Gln Asp Tyr Tyr Asn Leu
305                 310                 315                 320

Gly Gln Phe Thr Asp Asp Gln Val Pro Thr Pro Leu Val Ala Ile
                 325                 330                 335

Thr Ile Thr Arg Leu Val Val Gly Phe Leu Leu Pro Ser Val Ile Met
             340                 345                 350

Ile Ala Cys Tyr Ser Phe Ile Val Phe Arg Met Gln Arg Gly Arg Phe
         355                 360                 365

Ala Lys Ser Gln Ser Lys Thr Phe Arg Val Ala Val Val Val Val Ala
     370                 375                 380

Val Phe Leu Val Cys Trp Thr Pro Tyr His Ile Phe Gly Val Leu Ser
385                 390                 395                 400

Leu Leu Thr Asp Pro Glu Thr Pro Leu Gly Lys Thr Leu Met Ser Trp
                 405                 410                 415

Asp His Val Cys Ile Ala Leu Ala Ser Ala Asn Ser Cys Phe Asn Pro
             420                 425                 430

Phe Leu Tyr Ala Leu Leu Gly Lys Asp Phe Arg Lys Lys Ala Arg Gln
```

-continued

```
                435                    440                     445
Ser Ile Gln Gly Ile Leu Glu Ala Ala Phe Ser Glu Glu Leu Thr Arg
        450                    455                     460
Ser Thr His Cys Pro Ser Asn Asn Val Ile Ser Glu Arg Asn Ser Thr
465                    470                     475                     480
Thr Val
```

(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Trp Trp Gly Lys Lys Tyr Arg Ala Ser Lys Leu Gly Leu Ala Arg
1               5                   10                  15
```

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GAAGTGGTAC CATGGCGTC                          19

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GCTCCAAGCT TTCACACAGT TG                     22

THERAPEUTIC AND SCREENING METHODS USING C3A RECEPTOR AND C3A

This application claims the benefit of U.S. Provisional Application No. 60/019,627, filed Jun. 17, 1996.

This invention relates, in part, to method using newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human complement 3a receptor, hereinafter referred to as "C3a Receptor".

BACKGROUND OF THE INVENTION

During complement activation the 74–77 amino acid anaphylatoxins C3a, C4a and C5a are released. They are potent inflammatory mediators, inducing cellular degranulation, smooth muscle contraction, arachidonic acid metabolism, cytokine release, cellular chemotaxis (Reviewed in Gerard, C., and Gerard, N. P. (1994) *Annu. Rev. Immunol.* 12, 775–808; Hugli, T. E. (1984) *Springer Semin. Immunopathol.* 7, 193–219; Bitter-Suermann, D. (1988) in *The Complement System*, Ed. by K. Rother & G. Till, Springer Verlag, Heidelberg 367–395) and have been implicated in the pathogenesis of a number of inflammatory diseases (Vogt, W. (1986) *Complement* 3, 177–188; Morgan, B. P. (1994) *European J Clin Investigation* 24, 219–228). Studies have demonstrated the presence of a C3a receptor (C3a-R) on guinea pig platelets, rat mast cells, human neutrophils, eosinophils and platelets (Bitter-Suermann, D. (1988) in *The Complement System*, Ed. by K. Rother & G. Till, Springer Verlag, Heidelberg 367–395). A single class of high affinity C3a binding sites has been characterized on human neutrophils and differentiated U937 cells (Klos, A., Bank, S., Gietz, C., Bautsch, W., Köhl, J., Burg, M., and Kretzschmar, T. (1992) *Biochemistry* 31, 11274–11282). Competition binding and functional desensitization studies are consistent with the presence of a receptor for C3a which is distinct from the C5a-R (Bitter-Suermann, D. (1988) in *The Complement System*, Ed. by K. Rother & G. Till, Springer Verlag, Heidelberg 367–395; Klos, A., Bank, S., Gietz, C., Bautsch, W., Köhl, J., Burg, M., and Kretzschmar, T. (1992) *Biochemistry* 31, 11274–11282). However, there is evidence that C3a and C4a may bind to the same receptor as the two anaphylatoxins cross desensitize guinea pig ileal tissue (Hugli, T. E. (1984) *Springer Semin. Immunopathol.* 7, 193–219; Bitter-Suermann, D. (1988) in *The Complement System*, Ed. by K. Rother & G. Till, Springer Verlag, Heidelberg 367–395), although other investigators using guinea pig macrophages indicate that there may be separate receptors (Murakami, Y., Yamamoto, T., Imamichi, T., Nagasawa, S. (1993) *Immuol. Lett.* 36, 301–304). Functional activity of the C3a-R is sensitive to pertussis toxin, consistent with the binding site being composed of a GPCR (Klos, A., Bank, S., Gietz, C., Bautsch, W., Köhl, J., Burg, M., and Kretzschmar, T. (1992) *Biochemistry* 31, 11274–11282).

A complete understanding of the role of C3a in the pathogenesis of the inflammatory response has been hampered by the lack of ligand characterization of the cloned receptor. The present invention provides methods of using and functional characterization of human C3a receptor. This receptor was recently cloned from an HL-60 library by low-stringency screening with a fMetdeuPhe receptor probe. (Roglic, A., Prossnitz, E. R., et al. (1996) *Biochimica et Biophysica Acta* 1305, 3943). The report of this receptor contained no characterization of the receptor as a C3a receptor. Functional data on this important, useful feature was lacking in the report. It was characterized as an orphan receptor (AZ3B). Mouse L cells expressing AZ3B failed to bind and respond to the agonists examined, although C3a was not tested (Roglic, A., Prossnitz, E. R., et al. (1996) *Biochimica et Biophysica Acta* 1305, 39–43). The present invention provides important uses for the C3a receptor and compounds that agonize and antagonize C3a receptor function.

Clarification of this receptor as a C3a receptor and methods and compounds exploiting this important characterization are provided herein. Clearly, there is a need for factors that mediate inflammation and their roles in dysfunction and disease. There is a need, therefore, for identification and further characterization of such factors that mediate inflammation, and which can play a role in preventing, ameliorating or correcting dysfunctions or diseases.

The polypeptide used in the methods of the present invention has the conserved complement receptor residues, and have amino acid sequence homology to known complement receptors.

SUMMARY OF THE INVENTION

Toward these ends, and others, it is an object of the present invention to provide methods using polypeptides, inter alia, that have been identified as novel C3a Receptor by homology between the amino acid sequence set out in FIG. 1 and known amino acid sequences of other proteins such as set out in FIG. 2.

It is a further object of the invention, moreover, to provide methods using polynucleotides that encode C3a Receptor, particularly polynucleotides that encode the polypeptide herein designated C3a Receptor.

In a particularly preferred embodiment of this aspect of the invention the polynucleotide comprises the region encoding human C3a Receptor in the sequence set out in FIG. 1.

In accordance with this aspect of the present invention there are provided methods using an isolated nucleic acid molecule encoding a mature polypeptide expressed by the human cDNA contained in ATCC Deposit No. 75982.

In accordance with this aspect of the invention there are provided methods using isolated nucleic acid molecules encoding human C3a Receptor, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are methods using naturally occurring allelic variants of human C3a Receptor.

It also is an object of the invention to provide an agonist of the interaction of C3a and C3a Receptor.

Another object of the invention is an antibody against the interaction of C3a and C3a Receptor.

A further object of the invention is an antagonist which inhibits the interaction of C3a and C3a Receptor.

It also is an object of the invention to provide a method for the treatment of a patient having need of C3a Receptor comprising administering to the patient a therapeutically effective amount of C3a Receptor, said patient selected from the group consisting of acute inflammatory disease, atherosclerosis, chronic polyarthritis, systemic vasculitis, multiple sclerosis, Alzheimer's Disease, CNS inflammatory disease, Crohn's Disease, food allergies, non-bronchial allergies, osteoarthritis, osteoporosis, thyroid disease, and coronary heart disease.

It also is an object of the invention to provide a process for diagnosing a disease or a susceptibility to a disease related to expression of C3a Receptor comprising determining a mutation in the nucleic acid sequence encoding said polypeptide, said disease being selected from the group consisting of acute inflammatory disease, atherosclerosis, chronic polyarthritis, systemic vasculitis, multiple sclerosis, Alzheimer's Disease, CNS inflammatory disease, Crohn's Disease, food allergies, non-bronchial allergies, osteoarthritis, osteoporosis, thyroid disease, and coronary heart disease.

It is another object of the invention to provide a diagnostic process comprising analyzing for the presence of C3a Receptor in a sample derived from a host suspected of having a disease selected from the group consisting of acute inflammatory disease, atherosclerosis, chronic polyarthritis, systemic vasculitis, multiple sclerosis, Alzheimer's Disease, CNS inflammatory disease, Crohn's Disease, food allergies, non-bronchial allergies, osteoarthritis, osteoporosis, thyroid disease, and coronary heart disease.

It is yet another object of the invention to provide a method for identifying compounds which bind to and activate or inhibit the interaction of C3a and C3a Receptor comprising: contacting a cell expressing on the surface thereof a receptor for the polypeptide, said receptor being associated with a second component capable of providing a detectable signal in response to the binding of a compound to said receptor, with a compound to be screened under conditions to permit binding to the receptor; and determining whether the compound binds to and activates or inhibits the interaction of C3a and C3a Receptor by detecting the presence or absence of a signal generated from the interaction of C3a and C3a Receptor.

In accordance with still another embodiment of the present invention there is provided a process of using such activating compounds to stimulate the receptor polypeptide of the present invention for the treatment of conditions related to the under-expression of the C3a Receptor.

In accordance with another aspect of the present invention there is provided a process of using such inhibiting compounds for treating conditions associated with over-expression of the C3a Receptor.

In accordance with yet another aspect of the present invention there is provided non-naturally occurring synthetic, isolated and/or recombinant C3a Receptor polypeptides which are fragments, consensus fragments and/or sequences having conservative amino acid substitutions, of at least one transmembrane domain of the C3a Receptor of the present invention, such that the receptor may bind C3a Receptor ligands, or which may also modulate, quantitatively or qualitatively, C3a Receptor ligand binding.

In accordance with still another aspect of the present invention there are provided synthetic or recombinant C3a Receptor polypeptides, conservative substitution and derivatives thereof, antibodies, anti-idiotype antibodies, compositions and methods that can be useful as potential modulators of C3a Receptor function, by binding to ligands or modulating ligand binding, due to their expected biological properties, which may be used in diagnostic, therapeutic and/or research applications.

In accordance with another aspect of the present invention, there are provided C3a Receptor agonists. Among preferred agonists are molecules that mimic C3a Receptor, that bind to C3a or receptor molecules, and that elicit or augment C3a-induced responses. Also among preferred agonists are molecules that interact with C3a Receptor or C3a Receptor polypeptides, or with other modulators of C3a Receptor activities, and thereby potentiate or augment an effect of C3a Receptor or more than one effect of C3a Receptor.

In accordance with yet another aspect of the present invention, there are provided C3a Receptor antagonists. Among preferred antagonists are those which mimic C3a Receptor so as to bind to C3a Receptor or binding molecules but not elicit a C3a Receptor-induced response or more than one C3a Receptor-induced response. Also among preferred antagonists are molecules that bind to or interact with C3a Receptor so as to inhibit an effect of C3a Receptor or more than one effect of C3a Receptor or which prevent expression of C3a Receptor.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 (B) shows the predicted membrane topology of C3a Receptor. Amino acid residues in common between C5a receptor and C3a Receptor have been highlighted black, 2 predicted N-linked glycosylation sites, in the large extracellular loop and the amino and terminus, are indicated by grey shading.

FIGS. 2 (A–B) shows the regions of similarity between amino acid sequences of C3a Receptor (SEQ ID NO:2) and human C5a.

FIGS. 4 (C–D) shows cells expressing C3a Receptor but not C5a receptor bind and respond to C3a. Calcium mobilization by Fura 2 loaded cells expressing C5a receptor (FIGS. 4A & 4C) or C3a Receptor (FIGS. 4B & 4D) in response to rC5a (10 nM, FIG. 4A or 100 nM, FIG. 4B) or C3a analogue peptide (1 uM, FIGS. 4C & 4D).

FIG. 6 shows C3a Receptor cDNA sequence (SEQ ID NO: 1).

FIG. 7 shows C3a Receptor amino acid sequence (SEQ ID NO:2).

GLOSSARY

Figure 1B:
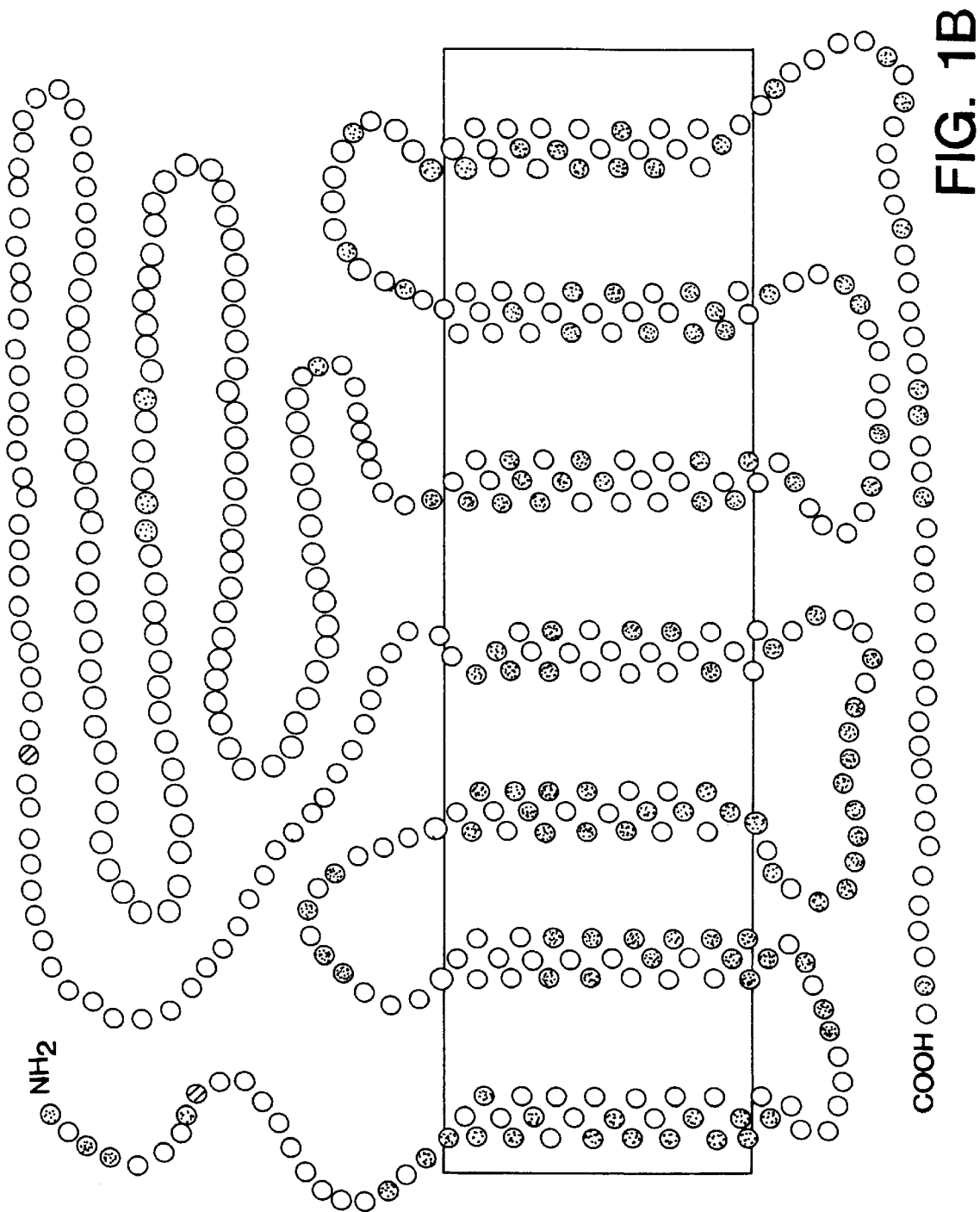
FIG. 1 (A) shows a nucleotide sequence and deduced amino acid sequence of C3a Receptor (SEQ ID NOS:1 & 2). The predicted seven membrane spanning domains of C3a Receptor are indicated by bold font and glycosylation sites are indicated by italics and underlines.

The following illustrative explanations are provided to facilitate understanding of certain terms used frequently herein, particularly in the examples. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 μg of plasmid or DNA fragment is digested with about 2 units of enzyme in about 20 μl of reaction buffer. For the purpose of isolating DNA fragments for plasmid construction, typically 5 to 50 μg of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

IDENTITY or SIMILARITY, as known in the art, are relationships between two polypeptides as determined by comparing the amino acid sequence and its conserved amino acid substitutes of one polypeptide to the sequence of a second polypeptide. Moreover, also known in the art is "identity" which means the degree of sequence relatedness between two polypeptide or two polynucleotides sequences as determined by the identity of the match between two strings of such sequences. Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity and similarity between two polynucleotide or polypeptide sequences, the terms "identity" and "similarity" are well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods commonly employed to determine identity or similarity between two sequences include, but are not limited to disclosed in Carillo, H., and Lipman, D., SIAM *J. Applied Math.*, 48: 1073 (1988). Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, J., et al., *Nucleic Acids Research* 12(1): 387 (1984)), BLASTP, BLASTN, FASTA (Atschul, S. F. et al., *J. Molec. Biol.* 215: 403 (1990)).

ISOLATED means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989) and Maniatis et al., pg. 146, as cited below.

OLIGONUCLEOTIDE(S) refers to relatively short polynucleotides. Often the term refers to single-stranded deoxyribonucleotides, but it can refer as well to single-or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLASMIDS generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., Analysis for protein modifications and nonprotein cofactors, Meth. Enzymol. 182: 626–646 (1990) and Rattan et al., Protein Synthesis: Posttranslational Modifications and Aging, Ann. N.Y. Acad. Sci. 663: 48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cell often carry out the same post-translational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

RECEPTOR MOLECULE, as used herein, refers to molecules of the present invention, including but not limited to C3a Receptor polypeptides, as well as molecules which bind or interact specifically with C3a Receptor polypeptides of the present invention, including not only classic receptors, which are preferred, but also other molecules that specifically bind to or interact with polypeptides of the invention (which also may be referred to as "binding molecules" and "interaction molecules," respectively and as "C3a Receptor binding molecules" and "C3a Receptor interaction molecules.") Binding between polypeptides of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

Receptors also may be non-naturally occurring, such as antibodies and antibody-derived reagents that bind specifically to polypeptides of the invention.

DESCRIPTION OF THE INVENTION

The present invention relates to methods using novel C3a Receptor polypeptides and polynucleotides, among other things, as described in greater detail below. In particular, the invention relates to methods using polypeptides and polynucleotides of a novel human C3a Receptor, which is related by amino acid sequence homology to C5a receptor polypeptide. The invention relates especially to methods using C3a Receptor having the nucleotide and amino acid sequences set out in FIG. 1, and to the C3a Receptor nucleotide and amino acid sequences of the human cDNA in ATCC Deposit No. 75982, which is herein referred to as "the deposited clone" or as the "cDNA of the deposited clone." It will be appreciated that the methods using nucleotide and amino acid sequences set out in FIG. 1 were obtained by sequencing the cDNA of the deposited clone. Hence, the sequence of the deposited clone is controlling as to any discrepancies between the two and any reference to the sequences of FIG. 1 include reference to the sequence of the human cDNA of the deposited clone.

Polynucleotides

In accordance with one aspect of the present invention, there are provided methods using isolated polynucleotides which encode the C3a Receptor polypeptide having the deduced amino acid sequence of FIG. 1.

Using the information provided herein, such as the polynucleotide sequence set out in FIG. 1, a polynucleotide of the methods of the present invention encoding human C3a Receptor polypeptide may be obtained using standard cloning and screening procedures, such as those for cloning cDNAs using mRNA from cells from microvascular endothelial tissue as starting material. Illustrative of the invention, the polynucleotide set out in FIG. 1 was discovered in a cDNA library derived from cells of human microvascular endothelial tissue.

Human C3a Receptor of the methods of invention is structurally related to other proteins of the complement receptor family, as shown by the results of sequencing the cDNA encoding human C3a Receptor in the deposited clone. The cDNA sequence thus obtained is set out in FIG. 1. It contains an open reading frame encoding a protein of about 482 amino acid residues. The protein exhibits significant homology to a known C5a receptor protein. C3a Receptor of FIG. 1 has about 26% identity and about 58% similarity with the amino acid sequence of C5a receptor. Oocytes and RBL-2H3 cells expressing C3a receptor respond to C3a and a C3a analogue synthetic peptide (See Examples below). Mammalian cells expressing this gene specifically bind C3a and the peptide analogue. In view of these data, along with the results of the tissue distribution analysis, this invention provides a human C3a receptor. The demonstration in the present invention that C3a receptor expression is not limited to myeloid cells, but that they both are expressed in a variety of non-myeloid cells throughout the body and that they are abundantly expressed in the central nervous system, indicates that these receptors play an important role in the pathogenesis of inflammatory and autoimmune diseases.

Polynucleotides used in methods of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIG. 1. It also may be a polynucleotide with a different sequence, which, as a result of the redundancy (degeneracy) of the genetic code, encodes the polypeptide of the DNA of FIG. 1.

Polynucleotides used in methods of the present invention which encode the polypeptide of FIG. 1 may include, but are not limited to the coding sequence for the mature polypeptide, by itself; the coding sequence for the mature polypeptide and additional coding sequences, such as those encoding a leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the pQE vector (Qiagen, Inc.), among others, many of which are commercially available. As described in Gentz et al., Proc. Natl. Acad. Sci., USA 86: 821–824 (1989), for instance, hexa-histidine provides for convenient purification of the fusion protein. The HA tag corresponds to an epitope derived of influenza hemagglutinin protein, which has been described by Wilson et al., Cell 37: 767 (1984), for instance.

In accordance with the foregoing, the term "polynucleotide encoding a polypeptide" as used herein encompasses polynucleotides which include a sequence encoding a polypeptide of the present invention, particularly the human C3a Receptor having the amino acid sequence set out in FIG. 1. The term also encompasses polynucleotides that include a single continuous region or discontinuous regions encoding the polypeptide (for example, interrupted by introns) together with additional regions, that also may contain coding and/or non-coding sequences.

The present invention further relates to methods using variants of the herein above described polynucleotides which encode for fragments, analogs and derivatives of the polypeptide having the deduced amino acid sequence of FIG. 1. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are methods using polynucleotides encoding polypeptides having the amino acid sequence of C3a Receptor set out in FIG. 1; variants, analogs, derivatives and fragments thereof, and fragments of the variants, analogs and derivatives.

Further particularly preferred in this regard are methods using polynucleotides encoding C3a Receptor variants, analogs, derivatives and fragments, and variants, analogs and derivatives of the fragments, which have the amino acid sequence of the C3a Receptor polypeptide of FIG. 1 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the C3a Receptor. Also especially preferred in this regard are conservative substitutions. Most highly preferred are polynucleotides encoding polypeptides having the amino acid sequence of FIG. 1, without substitutions.

Further preferred embodiments of the invention are methods using polynucleotides that are at least 70% identical to a polynucleotide encoding the C3a Receptor polypeptide having the amino acid sequence set out in FIG. 1, and polynucleotides which are complementary to such polynucleotides. Alternatively, most highly preferred are polynucleotides that comprise a region that is at least 80% identical to a polynucleotide encoding the C3a Receptor polypeptide of the human cDNA of the deposited clone and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this resect, moreover, are methods using polynucleotides which encode polypeptides which retain substantially the same biological function or activity as the mature polypeptide encoded by the cDNA of FIG. 1.

The present invention further relates to methods using polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for cDNA and genomic DNA to isolate full-length cDNAs and genomic clones encoding C3a Receptor and to isolate cDNA and genomic clones of other genes that have a high sequence similarity to the human C3a Receptor gene. Such probes generally will comprise at least 15 bases. Preferably, such probes will have at least 30 bases and may have at least 50 bases. Particularly preferred probes will have at least 30 bases and will have 50 bases or less.

For example, the coding region of the C3a Receptor gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the methods of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited materials

A deposit containing a human C3a Receptor cDNA has been deposited with the American Type Culture Collection, as noted above. Also as noted above, the human cDNA deposit is referred to herein as "the deposited clone" or as "the cDNA of the deposited clone."

The deposited clone was deposited with the American Type Culture Collection, 10801 University Boulevard, Manassas, Va., 20110-2209, USA, on Dec. 16, 1994, and assigned ATCC Deposit No. 75982.

The deposited material is a pBluescript SK (-) plasmid (Stratagene, La Jolla, Calif.) that contains the full length C3a Receptor cDNA.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to methods using a human C3a Receptor polypeptide which has the deduced amino acid sequence of FIG. 1.

The invention also relates to methods using fragments, analogs and derivatives of these polypeptides. The terms "fragment," "derivative" and "analog" when referring to the polypeptide of FIG. 1, means a polypeptide which retains essentially the same biological function or activity as such polypeptide, i.e. functions as a C3a Receptor, or retains the ability to bind the ligand or the receptor even though the polypeptide does not function as a C3a Receptor, for example, a soluble form of the receptor. Thus, an analog includes a proprotein which can be activated by cleavage of the proprotein portion to produce an active mature polypeptide.

The polypeptide of the methods of the present invention may be a recombinant polypeptide, a natural polypeptide or a synthetic polypeptide. In certain preferred embodiments it is a recombinant polypeptide.

The fragment, derivative or analog of the polypeptide of FIG. 1 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are methods using polypeptides having the amino acid sequence of C3a Receptor set out in FIG. 1, variants, analogs, derivatives and fragments thereof, and variants, analogs and derivatives of the fragments. Alternatively, particularly preferred embodiments of the invention in this regard are methods using polypeptides having the amino acid sequence of the C3a Receptor, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the C3a Receptor polypeptide of FIG. 1, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the C3a Receptor. Also especially preferred in this regard are conservative substitutions. Most highly preferred are polypeptides having the amino acid sequence of FIG. 1 without substitutions.

The polypeptides and polynucleotides of the methods of the present invention are preferably provided in an isolated form, and preferably are purified to homogeneity.

The polypeptides of the methods of the present invention include the polypeptide of SEQ ID NO:2 (in particular the mature polypeptide) as well as polypeptides which have at least 80% identity to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are methods using polypeptides comprising fragments of C3a Receptor, most particularly fragments of the C3a Receptor having the amino acid set out in FIG. 1, and fragments of variants and derivatives of the C3a Receptor of FIG. 1.

In this regard a fragment is a polypeptide having an amino acid sequence that entirely is the same as part but not all of the amino acid sequence of the aforementioned C3a Receptor polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a C3a Receptor polypeptide of the present comprised within a precursor polypeptide designed for expression in a host and having heterologous pre and pro-polypeptide regions fused to the amino terminus of the C3a Receptor fragment and an additional region fused to the carboxyl terminus of the fragment. Therefore, fragments in one aspect of the meaning intended herein, refers to the portion or portions of a fusion polypeptide or fusion protein derived from C3a Receptor.

As representative examples of polypeptide fragments of methods of the invention, there may be mentioned those which have from about 5–15, 10–20, 15–40, 30–55, 41–75, 41–80, 41–90, 50–100, 75–100, 90–115, 100–125, and 110–113 amino acids long.

In this context about includes the particularly recited range and ranges larger or smaller by several, a few, 5, 4, 3, 2 or 1 amino acid at either extreme or at both extremes. For instance, about 40–90 amino acids in this context means a polypeptide fragment of 40 plus or minus several, a few, 5, 4, 3, 2 or 1 amino acids to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 5–15, 10–20, 15–40, 30–55, 41–75, 41–80, 41–90, 50–100, 75–100, 90–115, 100–125, and 110–113 amino acids long.

Among especially preferred fragments of the methods of the invention are truncation mutants of C3a Receptor. Truncation mutants include C3a Receptor polypeptides having the amino acid sequence of FIG. 1, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are methods using fragments characterized by structural or functional attributes of C3a Receptor. Preferred embodiments of the invention in this regard include methods using fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of C3a Receptor.

Certain preferred regions in these regards are set out in FIG. 3, and include, but are not limited to, regions of the aforementioned types identified by analysis of the amino acid sequence set out in FIG. 1. As set out in FIG. 3, such preferred regions include Garnier-Robson alpha-regions, beta-regions, turn-regions and coil-regions, Chou-Fasman alpha-regions, beta-regions and turn-regions, Kyte-Doolittle hydrophilic regions and hydrophilic regions, Eisenberg alpha and beta amphipathic regions, Karplus-Schulz flexible regions, Emini surface-forming regions and Jameson-Wolf high antigenic index regions.

Among highly preferred fragments in this regard are those that comprise regions of C3a Receptor that combine several structural features, such as several of the features set out above. In this regard, the regions defined by the residues about 10 to about 20, about 40 to about 50, about 70 to about 90 and about 100 to about 113 of FIG. 1, which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of C3a Receptor. Most highly preferred in this regard are fragments that have a chemical, biological or other activity of C3a Receptor, including those with a similar activity or an improved activity, or with a decreased undesirable activity. Highly preferred in this regard are fragments that contain regions that are homologs in sequence, or in position, or in both sequence and to active regions of related polypeptides, such as the related polypeptides set out in FIG. 2, which include C5a receptor. Among particularly preferred fragments in these regards are truncation mutants, as discussed above.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Vectors, host cells, expression

The present invention also relates to vectors which include polynucleotides of the present invention, host cells which are genetically engineered with vectors Of the invention and the production of polypeptides of the invention by recombinant techniques.

Host cells can be genetically engineered to incorporate polynucleotides and express polypeptides of the present invention. For instance, polynucleotides may be introduced in to host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques. In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skilled in the art, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the $E.\ coli$ lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing $E.\ coli$ and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as $E.\ coli$, Streptomyces and $Salmonella\ typhimurium$ cells; fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

More particularly, the present invention also relates to recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, PHAGESCRIPT vectors, BLUESCRIPT vectors, pNH8A, pNH16a, pNH18A, pNH46A, available from Stratagene; and ptrc99a, pKK223-3, pKK233-3, pDR540, pRIT5 available from Phannacia. Among preferred eukayotic vectors are pWLNEO, pSV2CAT, pOG44, pXT1 and pSG available from Stratagene; and pSVK3, pBPV, pMSG and PSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the $E.\ coli$ lacI and lacZ promoters, the T3 and T7 promoters, the gpt promoter, the lambda PR, PL promoters and the tip promoter.

Among known eukaryotic promoters suitable in this regard are the CMV immediate early promoter, the HSV thymidine kinase promoter, the early and late SV40 promoters, the promoters of reroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of E. coli and the trp1 gene of S. cerevisiae.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunolglobulin that is useful to solubilize receptors. For example, EP-A-O 464 533 (Canadian counterpart 2045869) discloses fusion proteins comprising various portions of constant region of immunoglobin molecules together with another human protein or part thereof. In many cases, the Fc part in fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, shIL5-has been fused with Fc portions for the purpose of high-throughput screening assays to identify antagonists of hIL-5. See, D. Bennett et al., Journal of Molecular Recognition, Vol. 8 52–58 (1995) and K. Johanson et al., The Journal of Biological Chemistry, Vol. 270, No. 16, pp 9459–9471 (1995).

Suitable prokaryotic hosts for propagation, maintenance or expression of polynucleotides and polypeptides in accordance with the invention include Escherichia coli, Bacillus subtilis and Salmonella typhimurium. Various species of Pseudomonas, Streptomyces, and Staphylococcus are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-7 lines of monkey kidney fibroblast, described in Gluzman et al., Cell 23: 175 (1981). Other cell lines capable of expressing a compatible vector include for example, the C127, 3T3, CHO, HeLa, human kidney 293 and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The C3a Receptor polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

C3a Receptor polynucleotides and polypeptides may be used in accordance with the present invention for a variety of applications, particularly those that make use of the chemical and biological properties of C3a Receptor. Additional applications relate to diagnosis and to treatment of disorders of cells, tissues and organisms. These aspects of the invention are illustrated further by the following discussion.

Polynucleotide assays

This invention is also provides uses of the C3a Receptor polynucleotides to detect complementary polynucleotides such as, for example, as a diagnostic reagent. Detection of a mutated form of C3a Receptor associated with a dysfunction will provide a diagnostic tool that can add or define a diagnosis of a disease or susceptibility to a disease which results from under-expression over-expression or altered expression of C3a Receptor. Individuals carrying mutations in the human C3a Receptor gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. PCR (Saiki et al., Nature, 324: 163–166 (1986)). RNA or cDNA may also be used in the same ways. As an example, PCR primers complementary to the nucleic acid encoding C3a Receptor can be used to identify and analyze C3a Receptor expression and mutations. For example, deletions and insertions can be detected by a change in size of the amplified product in comparison to the normal genotype. Point mutations can be identified by hybridizing amplified DNA to radiolabeled C3a Receptor RNA or alternatively, radiolabeled C3a Receptor antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230: 1242 (1985)).

Sequence changes at specific locations also may be revealed by nuclease protection assays, such as RNase and S1 protection or the chemical cleavage method (e.g., Cotton et al., Proc. Natl. Acad. Sci., USA, 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

In accordance with a further aspect of the invention, there is provided a process for determining disease, including but not limited to, acute inflammatory disease, atherosclerosis, chronic polyarthritis, systemic vasculitis, multiple sclerosis, Alzheimer's Disease, CNS inflammatory disease, Crohn's Disease, food allergies, non-bronchial allergies, osteoarthritis, osteoporosis, thyroid disease, and coronary heart disease, or a susceptibility to the afformentioned diseases. Thus, a mutation in C3a Receptor indicates a susceptibility to disease, including but not limited to, acute inflammatory disease, atherosclerosis, chronic polyarthritis, systemic vasculitis, multiple sclerosis, Alzheimer's Disease, CNS inflammatory disease, Crohn's Disease, food allergies, non-bronchial allergies, osteoarthritis, osteoporosis, thyroid disease, and coronary heart disease, and the nucleic acid sequences described above may be employed in an assay for ascertaining such susceptibility. Thus, for example, the assay may be employed to determine a mutation in a human C3a Receptor protein as herein described, such as a deletion, truncation, insertion, frame shift, etc., with such mutation being indicative of a susceptibility to disease, including but not limited to, acute inflammatory disease, atherosclerosis, chronic polyarthritis, systemic vasculitis, multiple sclerosis, Alzheimer's Disease, CNS inflammatory disease, Crohn's Disease, food allergies, non-bronchial allergies, osteoarthritis, osteoporosis, thyroid disease, and coronary heart disease. Such processes are also useful to determine renal disease, for example, Systemic Lupus Erythematosis, SLE-associated nephritis, membranoproliferative GN, membranous nephritis; rheumatological diseases, for example, rheumatoid arthritis, SLE, Behcet's syndrome, juvenile rheumatoid arthritis, Sögren's syndrome; neurological diseases, for example, myasthenia gravis, multiple sclerosis, cerebral lupus, Guillain-Barre syndrome, Alzheimer's disease; dermatological diseases, for example, pernphigus/pemphigoid, phototoxic reactions, vasculitis; biocompatibility/shock diseases, for example, post-bypass syndrome, catheter reactions, sepsis, ARDS, anaphylaxis, transplant rejection, pre-eclampsia; and other diseases, for example, atheroma, bowel inflammation, thyroiditis, and infertility, susceptibility to pyogenic infections, glomerulonephritis, suseptibility to neisserial infections, recurrent subcutaneous swelling and mucosal oedema, and recurrent episodes of thrombosis/haemolysis.

A mutation may be ascertained for example, by a DNA sequencing assay. Tissue samples, including but not limited to blood samples are obtained from a human patient. The samples are processed by methods known in the art to capture the RNA. First strand cDNA is synthesized from the RNA samples by adding an oligonucleotide primer consisting of polythymidine residues which hybridize to the polyadenosine stretch present on the mRNA's. Reverse transcriptase and deoxynucleotides are added to allow synthesis of the first strand cDNA. Primer sequences are synthesized based on the DNA sequence of the DNA repair protein of the invention. The primer sequence is generally comprised of at least 15 consecutive bases, and may contain at least 30 or even 50 consecutive bases.

RT-PCR can also be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding C3a Receptor can be used to identify and analyze mutations. Examples of representative primers are shown below in Table 1. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Using the sequences provided herein, skilled artisans will be able to readily prepare polynucleotide amplification primers.

Polynucleotide primers may be used for amplifying C3a Receptor cDNA isolated from a sample derived from a patient. The primers may be used to amplify the gene isolated from the patient such that the gene may then be subject to various techniques for elucidation of the DNA sequence. In this way, mutations in the DNA sequence may be diagnosed.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and SI protection or the chemical cleavage method (e.g., Cotton et al., PNAS, USA, 85:4397–4401 (1985)).

Thus, the detection of a specific DNA sequence and/or quantitation of the level of the sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA. The invention provides a process for diagnosing, disease, particularly disease, including but not limited to, acute inflammatory disease, atherosclerosis, chronic polyarthritis, systemic vasculitis, multiple sclerosis, Alzheimer's Disease, CNS infammatory disease, Crohn's Diease, food allergies, non-bronchial allergies, osteoarthritis, osteoporosis, thyroid disease, coronary heart disease, Systemic Lupus Erythematosis, SLE-associated nephritis, membranoproliferative GN, membranous nephritis; rheumatological diseases, for example, rheumatoid arthritis, SLE, Behcet's syndrome, juvenile rheumatoid arthritis, Sjögren's syndrome; neurological diseases, for example, myasthenia gravis, multiple sclerosis, cerebral lupus, Guillain-Barre syndrome, Alzheimer's disease; dermatological diseases, for example, pernphigus/pemphigoid, phototoxic reactions, vasculitis; biocompatibility/shock diseases, for example, post-bypass syndrome, catheter reactions, sepsis, ARDS, anaphylaxis, transplant rejection, pre-eclampsia; and other diseases, for example, atheroma, bowel inflammation, thyroiditis, and infertility, suseptibility to pyogenic infections, glomerulonephritis, suseptibility to neisserial infections, recurrent subcutaneous swelling and mucosal oedema, and recurrent episodes of thrombosis/haemolysis, comprising determining from a sample derived from a patient a decreased level of expression of polynucleotide having the sequence of FIG. 1 (SEQ ID NO: 1).

Decreased expression of polynucleotide can be measured using any on of the methods well known in the art for the quantitation of polynucleotides, such as, for example, PCR, RT-PCR, RNase protection, Northern blotting and other hybridization methods.

In addition to more conventional gel-electrophoresis and DNA sequencing, mutations can also be detected by in situ analysis.

Polypeptide assays

The present invention also relates to a diagnostic assays such as quantitative and diagnostic assays for detecting levels of C3a Receptor protein in cells and tissues, including determination of normal and abnormal levels. Thus, for instance, a diagnostic assay in accordance with the invention for detecting over-expression of C3a Receptor protein compared to normal control tissue samples may be used to detect the presence of a tumor, for example. Assay techniques that can be used to determine levels of a protein, such as an C3a Receptor protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to C3a Receptor, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample is removed from a host and incubated on a solid support, e.g., a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any C3a Receptor proteins attached to the polystyrene dish. Unbound monoclonal antibody is washed out with buffer. The reporter antibody linked to horseradish peroxidase is placed in the dish resulting in binding of the reporter antibody to any monoclonal antibody bound to C3a Receptor. Unattached reporter antibody is then washed out. Reagents for peroxidase activity, including a colorimetric substrate are then added to the dish. Immobilized peroxidase, linked to C3a Receptor through the primary and secondary antibodies, produces a colored reaction product. The amount of color developed in a given time period indicates the amount of C3a Receptor protein present in the sample. Quantitative results typically are obtained by reference to a standard curve.

A competition assay may be employed wherein antibodies specific to C3a Receptor attached to a solid support and labeled C3a Receptor and a sample derived from the host are passed over the solid support and the amount of label detected attached to the solid support can be correlated to a quantity of C3a Receptor in the sample.

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., Nature 256: 495497 (1975), the trioma technique, the human B-cell hybridoma technique (Kozbor et al., Immunology Today 4: 72 (1983) and the EBV-hybridoma technique to produce human monoclonal antibodies (Cole et al., pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Thus, among others, antibodies against C3a Receptor may be employed to inhibit acute inflammatory disease, atherosclerosis, chronic polyarthritis, systemic vasculitis, multiple sclerosis, Alzheimer's Disease, CNS inflammatory disease, Crohn's Disease, food allergies, non-bronchial allergies, osteoarthritis, osteoporosis, thyroid disease, coronary heart disease; renal disease, for example, Systemic Lupus Erythematosis, SLE-associated nephritis, membranoproliferative GN, membranous nephritis; rheumatological diseases, for example, rheumatoid arthritis, SLE, Behcet's syndrome, juvenile rheumatoid arthritis, Sjögren's syndrome; neurological diseases, for example, myasthenia gravis, multiple sclerosis, cerebral lupus, Guillain-Barre syndrome, Alzheimer's disease; dermatological diseases, for example, pernphigus/pemphigoid, phototoxic reactions, vasculitis; biocompatibility/shock diseases, for example, post-bypass syndrome, catheter reactions, sepsis, ARDS, anaphylaxis, transplant rejection, pre-eclampsia; and other diseases, for example, atheroma, bowel inflammation, thyroiditis, and infertility, suseptibility to pyogenic infections, glomerulonephritis, suseptibility to neisserial infections, recurrent subcutaneous swelling and mucosal oedema, and recurrent episodes of thrombosis/haemolysis.

C3a Receptor binding molecules and assays

This invention also provides a method for identification of molecules, such as receptor molecules, that bind C3a Receptor. Genes encoding proteins that bind C3a Receptor or inhibit the activation of C3a analogs or C3 mimetics of C3a Receptor by C3a, such as receptor proteins, can be identified by numerous methods known to those of skill in the art, for example, binding assays, competition studies, ligand panning and FACS sorting. Such methods are described in many laboratory manuals such as, for instance, Coligan et al., Current Protocols in Immunology 1(2): Chapter 5 (1991).

For instance, expression cloning may be employed for this purpose. To this end polyadenylated RNA is prepared from a cell responsive to C3a, a cDNA library is created from this RNA, the library is divided into pools and the pools are transfected individually into cells that are not responsive to C3a. The transfected cells then are exposed to labeled C3a. (C3a can be labeled by a variety of well-known techniques including standard methods of radio-iodination or inclusion of a recognition site for a site-specific protein kinase.) Following exposure, the cells are fixed and binding of C3a to the C3a Receptor is determined. These procedures conveniently are carried out on glass slides.

Pools are identified of cDNA that produced C3a Receptor-binding cells. Sub-pools are prepared from these positives, transfected into host cells and screened as described above. Using an iterative sub-pooling and re-screening process, one or more single clones that encode the putative binding molecule, such as a receptor molecule, can be isolated.

Alternatively a labeled ligand, such as, for example, C3a, can be photoaffinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor, such as C3a-C3a Receptor complex, can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides used in the methods of the invention also can be used to assess C3a such as receptor molecules, in cells or in cell-free preparations.

The C3a Receptor of the present invention may be employed in a process for screening for compounds which activate (agonists) or inhibit its activation (antagonists) by C3a.

In general, such screening procedures involve providing appropriate cells which express the C3a Receptor polypeptide of the present invention on the surface thereof. Such cells include cells from mammals, yeast, drosophila or *E. Coli*. In particular, a polynucleotide encoding the C3a Receptor of the present invention is employed to transfect cells to thereby express the C3a Receptor. The expressed receptor is then contacted with a test compound and C3a to observe binding, stimulation or inhibition of a functional response.

One such screening procedure involves the use of melanophores which are transfected to express the C3a Receptor of the present invention. Such a screening technique is described in PCT WO 92/01810 published Feb. 6, 1992.

Thus, for example, such assay may be employed for screening for a compound which inhibits activation of the receptor polypeptide of the present invention by contacting the melanophore cells which encode the receptor with both the C3a and a compound to be screened. Inhibition of the signal generated by C3a indicates that a compound is a potential antagonist for the receptor, i.e., inhibits activation of the receptor by C3a.

The screen may be employed for determining a compound which activates the receptor by contacting such cells with compounds to be screened and determining whether such compound generates a signal, i.e., activates the receptor.

Other screening techniques include the use of cells which express the C3a Receptor (for example, transfected CHO cells) in a system which measures extracellular pH changes caused by receptor activation, for example, as described in Science, volume 246, pages 181–296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the C3a Receptor into Xenopus oocytes to transiently express the receptor. The receptor oocytes may then be contacted with the receptor ligand and a compound to be screened, followed by detection of inhibition or activation of a signal in the case of screening for compounds which are thought to inhibit activation of the receptor by C3a.

Another screening technique involves expressing the C3a Receptor in which the receptor is linked to a signal transduction system, e.g., "a phospholipase C or D or other proteins. As representative examples of such cells, there may be mentioned endothelial cells, smooth muscle cells, embryonic kidney cells, 293 cells, and cells set forth in the Examples hereto. The screening may be accomplished as hereinabove described by detecting activation of the receptor or inhibition of activation of the receptor from a second signal, such as for example phospholipase or other activated/expressed protein.

Another method involves screening for compounds which inhibit activation of the receptor polypeptide of the present invention antagonists by determining inhibition of binding of labeled C3a to cells which have the receptor on the surface thereof. Such a method involves transfecting a eukaryotic cell with DNA encoding the C3a Receptor such that the cell expresses the receptor on its surface and contacting the cell with a compound in the presence of a labeled form of C3a. The ligand can be labeled, e.g., by radioactivity. The amount of labeled C3a bound to the receptors is measured, e.g., by measuring radioactivity of the receptors. If the compound binds to the receptor as determined by a reduction of labeled C3a which binds to the receptors, the binding of labeled C3a to the receptor is inhibited.

Yet another screening technique involves the use of well known FLIPR equipment for high throughput screening of test compounds that mobilize intracellular calcium ions, or other ions or membrane charge changes, through the compound's effect on the C3a receptor. Preferred ions to be detected are those capable of being detected with dyes. Membrane charge changes can also be detected with well known charge-sensitive dyes.

Still another screening technique involves the use of FLIPR equipment for high throughput screening of test compounds that inhibit mobilization of intracellular calcium ions, or other ions, by affecting the interaction of C3a and C3a Receptor.

As used herein, C3a means natural and recombinant C3a ligand and C3a analogs.

C3a Receptor are ubiquitous in the mammalian host and are responsible for many biological functions, including many pathologies. Accordingly, it is desirous to find compounds and drugs which stimulate the C3a Receptor or the interaction of C3a and C3a Receptor on the one hand and which can inhibit the function of a C3a Receptor on the other hand.

For example, compounds which activate the C3a Receptor or the interaction of C3a and C3a Receptor may be employed for therapeutic purposes, such as the treatment of disease, including but not limited to, acute inflammatory disease, atherosclerosis, chronic polyarthritis, systemic vasculitis, multiple sclerosis, Alzheimer's Disease, CNS inflammatory disease, Crohn's Disease, food allergies, non-bronchial allergies, ostoartritis, osteoporosis, thyroid disease, coronary heart disease renal disease, for example, Systemic Lupus Erythematosis, SLE-associated nephritis, membranoproliferative GN, membranous nephritis; rheumatological diseases, for example, rheumatoid arthritis, SLE, Behcet's syndrome, juvenile rheumatoid arthritis, Sjögren's syndrome; neurological diseases, for example, myasthenia gravis, multiple sclerosis, cerebral lupus, Guillain-Barre syndrome, Alzheimer's disease; dermatological diseases, for example, pernphigus/pemphigoid, phototoxic reactions, vasculitis; biocompatibility/shock diseases, for example, post-bypass syndrome, catheter reactions, sepsis, ARDS, anaphylaxis, transplant rejection, pre-eclampsia; and other diseases, for example, atheroma, bowel inflammation, thyroiditis, and infertility, suseptibility to pyogenic infections, glomerulonephritis, suseptibility to neisserial infections, recurrent subcutaneous swelling and mucosal oedema, and recurrent episodes of thrombosis/haemolysis. As used herein, the phrase "interaction of C3a and C3a Receptor" includes physical interation as well as a functional or physiological response of C3a Receptor in a cell or cell-free system upon such cell or cell-free system being contacted by C3a.

In general, compounds which inhibit activation of the C3a Receptor may be employed for a variety of therapeutic purposes, for example, for the treatment of disease, including but not limited to, acute inflammatory disease, atherosclerosis, chronic polyarthritis, systemic vasculitis, multiple sclerosis, Alzheimer's Disease, CNS inflammatory disease, Crohn's Disease, food allergies, non-bronchial allergies, osteoarthritis, osteoporosis, thyroid disease, and coronary heart disease, among others. Compounds which inhibit C3a Receptor have also been useful in reversing disease, including but not limited to, acute inflammatory disease, atherosclerosis, chronic polyarthritis, systemic vasculitis, multiple sclerosis, Alzheimer's Disease, CNS inflammatory disease, Crohn's Disease, food allergies, non-bronchial allergies, osteoarthritis, osteoporosis, thyroid disease, coronary heart disease; renal disease, for example, Systemic Lupus Erythematosis, SLE-associated nephritis, membranoproliferative GN, membranous nephritis; rheumatological diseases, for example, rheumatoid arthritis, SLE, Behcet's syndrome, juvenile rheumatoid arthritis, Sjögren's syndrome; neurological diseases, for example, myasthenia gravis, cerebral lupus, Guillain-Barre syndrome; dermatological diseases, for example, pernphigus/pemphigoid, phototoxic reactions, vasculitis; biocompatibility/shock diseases, for example, post-bypass syndrome, catheter reactions, sepsis, ARDS, anaphylaxis, transplant rejection, pre-eclampsia; and other diseases, for example, atheroma, bowel inflammation, thyroiditis, and infertility, suseptibility to pyogenic infections, glomerulonephritis, suseptibility to neisserial infections, recurrent subcutaneous swelling and mucosal oedema, and recurrent episodes of thrombosis/haemolysis.

An antibody may antagonize a C3a Receptor of the present invention, or in some cases an oligopeptide, which bind to the C3a Receptor but does not elicit a second messenger response such that the activity of the C3a Receptor is prevented. Antibodies include anti-idiotypic antibodies which recognize unique determinants generally associated with the antigen-binding site of an antibody. Potential antagonist compounds also include proteins which are closely related to the ligand of the C3a Receptor, i.e. a fragment of the ligand, which have lost biological function and when binding to the C3a Receptor, elicit no response.

An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., *Nucl. Acids Res.,* 6:3073 (1979); Cooney et al, Science, 241:456 (1988); and Dervan et al., *Science,* 251: 1360 (1991)), thereby preventing transcription and the production of C3a Receptor. The antisense RNA oligonucleotide hybridizes to the mRNA in vivo and blocks translation of mRNA molecules into C3a Receptor (antisense—Okano, *J. Neurochem.,* 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of C3a Receptor.

A small molecule which binds to the C3a Receptor, making it inaccessible to C3a, or inhibiting the interaction of C3a and C3a Receptor, such that normal biological activity is prevented, for example small peptides or peptide-like molecules, may also be used to inhibit activation of the receptor polypeptide of the present invention.

A soluble form of the C3a Receptor, e.g. a fragment of the receptors, may be used to inhibit activation of the receptor by binding to C3a and preventing the interaction of C3a and C3a Receptor.

This invention additionally provides a method of treating an abnormal condition related to an excess of C3a Receptor activity which comprises administering to a subject the inhibitor compounds as hereinabove described along with a pharmaceutically acceptable carrier in an amount effective to inhibit activation by blocking binding of C3a to, or inhibiting the interaction of C3a and C3a Receptor with to the C3a Receptor, or by inhibiting a second signal, and thereby alleviating the abnormal conditions.

The invention also provides a method of treating abnormal conditions related to an under-expression of C3a Receptor activity which comprises administering to a subject a therapeutically effective amount of a compound which activates the receptor polypeptide of the present invention as described above in combination with a pharmaceutically acceptable carrier, to thereby alleviate the abnormal conditions.

The soluble form of the C3a Receptor, and compounds which activate or inhibit such receptor, may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

Agonists and antagonists—assays and molecules

The invention also provides a method of screening compounds to identify those which enhance or block the action of C3a Receptor on cells, such as its interaction with C3a Receptor-binding molecules such as C3a. An agonist is a compound which increases the natural biological functions of C3a Receptor or which functions in a manner similar to C3a Receptor or which enhance the interaction of C3a and C3a Receptor, while antagonists decrease or eliminate such functions.

For example, a cellular compartment, such as a membrane or a preparation thereof, such as a membrane-preparation, may be prepared from a cell that expresses a molecule that binds C3a Receptor, such as a molecule of a signaling or regulatory pathway modulated by C3a Receptor. The preparation is incubated with labeled C3a Receptor in the absence or the presence of a candidate molecule which may be a C3a Receptor agonist or antagonist. The ability of the candidate molecule to bind the binding molecule is reflected in decreased binding of the labeled ligand. Molecules which bind gratuitously, i.e., without inducing the effects of C3a Receptor on binding the C3a Receptor binding molecule, are most likely to be good antagonists. Molecules that bind well and elicit effects that are the same as or closely related to C3a Receptor are agonists.

C3a Receptor-like effects of potential agonists and antagonists may by measured, for instance, by determining activity of a second messenger system following interaction of the candidate molecule with a cell or appropriate cell preparation, and comparing the effect with that of C3a Receptor or molecules that elicit the same effects as C3a Receptor. Second messenger systems that may be useful in this regard include but are not limited to AMP guanylate cyclase, ion channel or phosphoinositide hydrolysis second messenger systems.

Another example of an assay for C3a Receptor antagonists is a competitive assay that combines C3a Receptor and a potential antagonist with membrane-bound C3a Receptor molecules or recombinant C3a Receptor molecules under appropriate conditions for a competitive inhibition assay. C3a Receptor can be labeled, such as by radioactivity, such that the number of C3a Receptor molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing C3a Receptor-induced activities, thereby preventing the action of C3a Receptor by excluding C3a Receptor from binding.

Potential antagonists include a small molecule which binds to and occupies the binding site of the polypeptide thereby preventing binding to cellular binding molecules, such as receptor molecules, such that normal biological activity is prevented. Examples of small molecules include but ate not limited to small organic molecules, peptides or peptide-like molecules.

Other potential antagonists include antisense molecules. Antisense technology can be used to control gene expression through antisense DNA or RNA or through triple-helix formation. Antisense techniques are discussed, for example, in—Okano, J. Neurochem. 56: 560 (1991); OUGODEOXY-NUCLEOTIDES AS ANTISENSE INVESTORS OF GENE EXPRESSION, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of C3a Receptor. The antisense RNA oligonucleotide hybridizes to the mRNA in vivo and blocks translation of the mRNA molecule into C3a Receptor polypeptide. The oligonucleotides described above can also be delivered to cells such that the antisense RNA or DNA may be expressed in vivo to inhibit production of C3a Receptor.

The antagonists may be employed in a composition with a pharmaceutically acceptable carrier, e.g., as hereinafter described.

The antagonists may be employed for instance to inhibit activation of the C3a Receptor by C3a for therapeutic purposes, for example, for the treatment of hypertension, angina pectoris, myocardial infarction, ulcers, Alzheimer's disease, stroke, inflammation (chronic and acute), CNS inflammation, asthma, allergies, neurodegenerative disease, head injury induced neurodegenerative disease, benign prostatic hypertrophy and psychotic and neurological disorders, including schizophrenia, manic excitement, depression, delirium, dementia or severe mental retardation, dyskinesias, such as Huntington's disease or Gilles dela Tourett's syndrome, among others. Compounds which inhibit G-protein coupled receptors have also been useful in reversing endogenous anorexia and in the control of bulimia.

The agonists may be employed in a composition with a pharmaceutically acceptable carrier, e.g., as hereinafter described.

The agonists may be employed for instance for therapeutic purposes, such as the treatment of asthma, Parkinson's disease, acute heart failure, hypotension, urinary retention, and osteoporosis.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 μg/kg body weight. In most cases they will be administered in an amount not in excess of about 8 mg/kg body weight per day. Preferably, in most cases, dose is from about 10 μg/kg to about 1 mg/kg body weight, daily. It will be appreciated that optimum dosage will be determined by standard methods for each treatment modality and indication, taking into account the indication, its severity, route of administration, complicating conditions and the like.

Gene therapy

The C3a Receptor polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in wvo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller et al., Biotechniques 7: 980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E86, GP+envAm12, and DAN cell lines as described in Miller, A., Human Gene Therapy 1: 5–14 (1990). The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The trasduced eukaryotic cells will express the nucleic acid sequence(s) encoding the polypeptide. Eukaryotic cells which may be transuded include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989), herein referred to as "Sambrook."

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook and numerous other references such as, for instance, by Goeddel et al., Nucleic Acids Res. 8: 4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 µg of DNA.

Example 1 cDNA Cloning cDNA library construction and screening were carried out essentially as described (Jelinek, L. J. Lok, S., Rosenberg, G. B., Smith, R. A., Grant, F. J., Biggs, S., Bensch, P. A., Kuijper, J. L., Sheppard, P. O., Sprecher, C. A., O'Hara, P. J., Foster, D., Walker, K. M., Chen, L. H. J., McKeman, P. A., and Kindsvogel, W. (1993) Science 259, 1614–1616), and DNA sequence was determined using a ABI sequencer (Adams, M. D., et al (1991) Science 252, 1651–1656). Expressed sequence tag (EST) analysis (Adams, M. D., et al (1991) Science 252, 1651–1656; Adams, M. D., et al (1992) Nature 355, 632–634; Adams, M. D., et al (1995) Nature 377 (suppl.) 3–174) of cDNA clones derived from a human neutrophil (LPS activated) cDNA library (oligo-dT primed and constructed in the lambda Uni-ZAP XR vector (Stratagene)) identified a clone demonstrating significant homology (approximately 40% amino acid sequence identity) to the C5a-R (Gerard, N. P. & Gerard, C. (1991) Nature 349, 614–617; Boulay, P., et al (1991) Biochemistry 30, 2993–2999). This cDNA clone contained an incomplete open reading frame (ORF) and therefore was used to re-probe the neutrophil cDNA library to obtain a full length cDNA. The alignment of C3a Receptor and the C5a-R was determined by the method of Needleman and Wunsch using the Gap comparison program of the Wisconsin Package, Version 8, September 1994, Genetics Computer Group, 575 Science Drive, Madison, Wis., USA 53711

Expressed sequence tag (ESI) analysis (Adams, M. D., et al (1991) Science 252, 1651–1656; Adams, M. D., et al (1992) Nature 355, 632–634; Adams, M. D., et al (1995) Nature 377 (suppl.) 3–174) of cDNA clones derived from a human neutrophil (LPS activated) cDNA library identified a clone demonstrating significant homology (approximately 40% amino acid sequence identity) to the C5a-R. This EST contained an incomplete open reading frame that therefore was used to re-probe the neutrophil cDNA library to obtain a 2040 bp cDNA encoding a complete orphan GPCR of 482 amino acids which shared 37% nucleotide identity, throughout the coding regions, with the C5a-R (FIG. 1A). Although similar to the C5a-R, this cDNA contains two predicted extracellular N-linked glycosylation sites and an unusually large extracellular domain between transmembrane domains 4 and 5 comprised of over 160 amino acid residues (FIG. 1A). The majority of the identical residues between the C5a-R and C3A Receptor reside in the predicted transmembrane spanning domains, and in the second intracellular loop (FIG. 1B).

Example 2

Northern Blot Analysis

Commercially prepared (Clontech, Palo Alto, Calif.) multiple tissue blots containing approximately 2 µg poly-A mRNA per lane were sequentially hybridized with random primer $^{32}$P-labeled cDNAs spanning the coding regions of C5a-R and C3a Receptor. C5a-R was cloned via PCR from differentiated U937 RNA. Final washing step was carried out twice in 0.5× SSC, 1% SDS at 65° C. for 20 min.

By Northern blot analysis, expression of C3a Receptor in human tissues and cell lines is distinct from C5a-R expression. An ~2.2 kilobase (kb) C5a-R transcript was abundantly expressed in peripheral blood leukocytes (PBL), lung, spleen, heart, placenta, spinal cord and throughout the brain. An ~2.1 kb C3a Receptor transcript was predominantly expressed in lung, spleen, ovary, placenta, small intestine, throughout the brain and to a much lesser extent than C5a-R, in heart and PBL. Although by Northern blot analysis the specific cells within the various tissues examined which are expressing C5a-R and C3a Receptor can't be determined, these data are suggestive that these receptors are abundantly expressed throughout the body. By fluorescent activated cell sorting using polyclonal antibodies generated to fusion proteins composed of glutathione S-transferase or maltose binding protein and the extracellular loop, this receptor has been shown to be expressed on several cell types, including U937, HL-60, PBL and human neutrophils and monocytes (Roglic, A., et al (1996) Biochimica et Biophysica Acta 1305, 39–43).

Example 3

Receptor expression and functional studies in Xenopus oocytes

Capped cRNA transcripts were generated from linearized C3a Receptor and C5a-R plasmid DNA as previously described (Kumar, C. S., et al (1989) J. Biol. Chem. 264, 17939–17946) and suspended in sterile water at a concentration of 0.2 µg/µl. Ovarian lobes were surgically removed from adult female Xenopus laevis frogs and defolliculated Stage V oocytes were harvested by manual dissection (Smith, L. D., et al (1991) Methods in Cell Biology, 36, 45–54. Edited by B. K. Kay and H. B. Peng, Academic Press Inc., New York.). Oocytes were microinjected with C3a Receptor or C5a-R cRNA transcripts (10 ng/oocyte) with or without U937 total RNA (25 ng/oocyte) in a 50 nl volume using a Drummond microinjection apparatus and maintained in modified Barth's saline (Power, C. A., et al (1995) J. Biol. Chem., 270,19495–19500 ) at 18° C. Electrophysiological recordings from an average of 10 oocytes were made 48 h later at room temperature using the two electrode voltage clamp (Warner Instruments) technique. Membrane potentials were routinely clamped at −60 mV. Results represent average response determined in three separate experiments.

The chemotactic receptors for C5a and the fMLP-R have previously been functionally expressed in Xenopus laevis oocytes (Kroll, B., et al (1991) FEBS Lett. 291, 208–210; Murphy, P. M. & McDermott, D. (1991) J Biol. Chem. 266, 12560–12567; Murphy, P. M., Gallin, E. K., and Tiffany, H. L. (1990) J Immunol. 145, 2227–2234; Schultz, P., et al (1992) Cellular Signalling 4, 153–161) and, unlike all other GPCRs tested in this system, injection of cRNA for the cloned chemotactic receptors alone is insufficient to stimulate signal transduction in response to ligand binding (Kroll, B., et al (1991) FEBS Lett. 291, 208–210; Murphy, P. M. & McDermott, D. (1991) J Biol. Chem. 266, 12560–12567). Functional expression of both of these chemotactic receptors, as monitored by induction of $Ca^{2+}$ mediated chloride currents, requires the co-injection of a complimentary human factor which can be supplied by total RNA from myeloid or liver cells (Kroll, B., et al (1991) FEBS Lett. 291, 208–210; Murphy, P. M. & McDermott, D. (1991) J Biol.

Figure 3A:
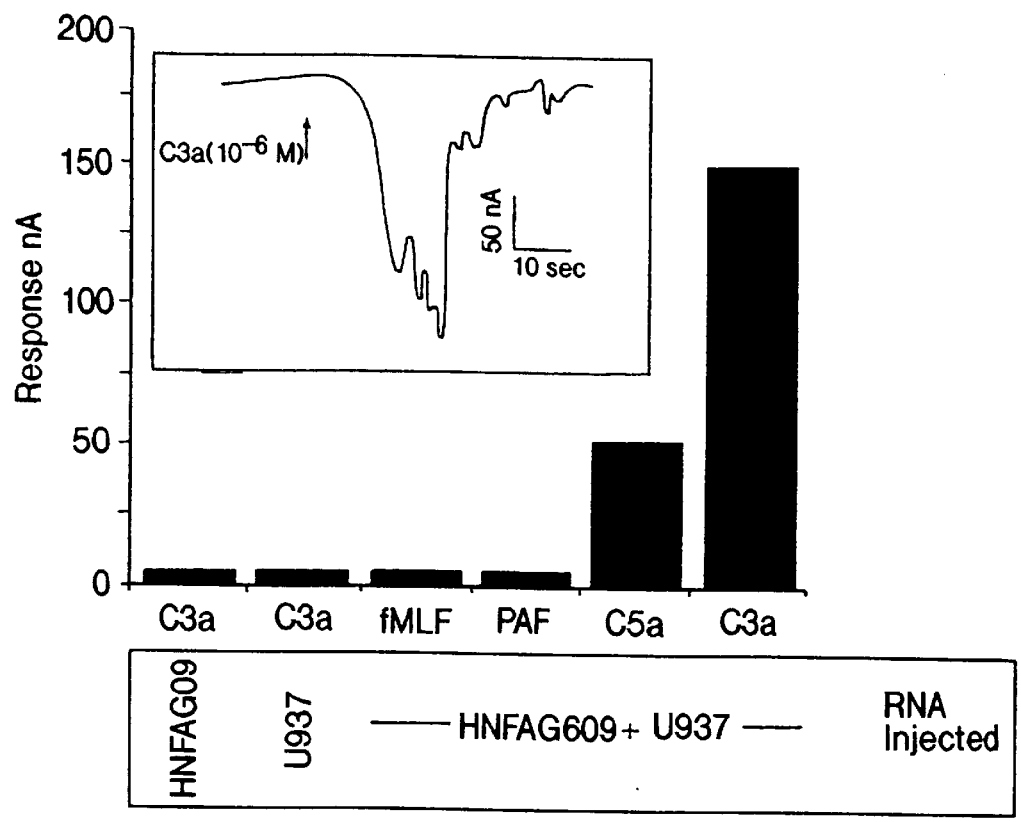
FIGS. 3 (A–B) shows that C5a receptor and C3a Receptor transcripts are abundantly expressed in the central nervous system and throughout the body. Tissue distribution of C5a receptor and C3a Receptor as determined by Northern blot analysis. Tissue source of RNA indicated above each lane.
Figure 3B:
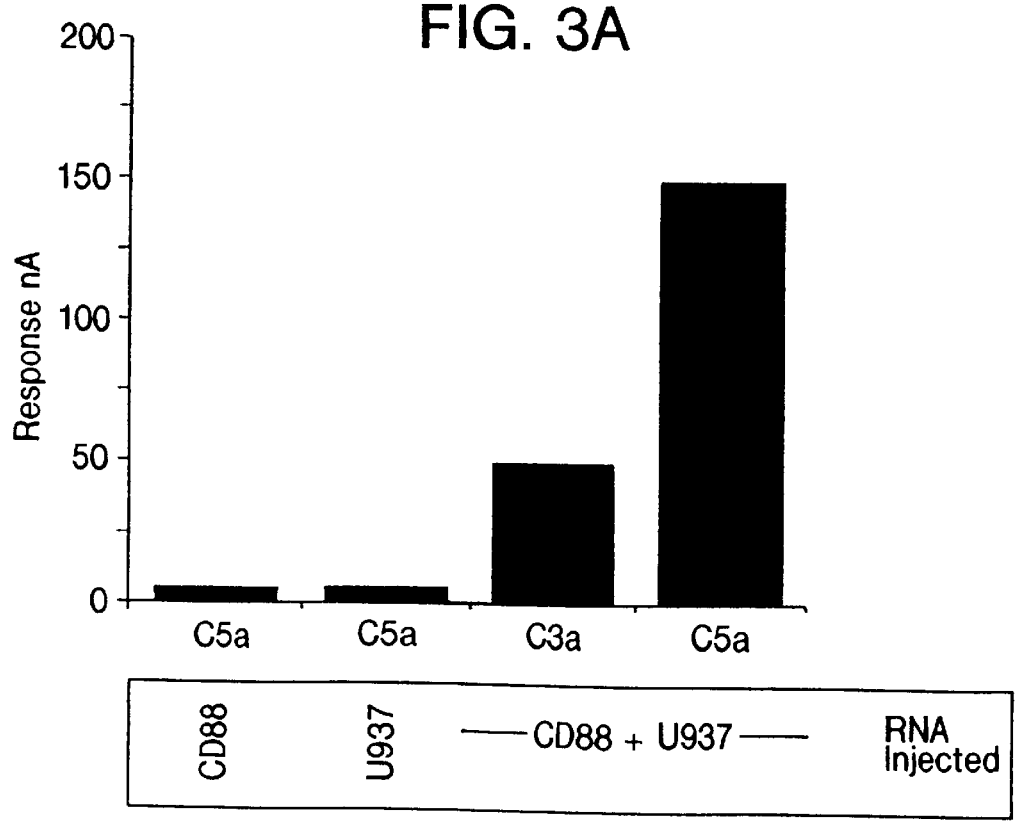

Chem. 266, 12560–12567). The co-factor is required for receptor-mediated signal transduction but not for expression of the C5a-R or fMLF-R on the surface of the oocytes (Murphy, P. M., et al (1990) *J Immunol.* 145, 2227–2234). The nature of the co-factor is unknown but it does not appear to be an alpha subunit of $G_{i1}$, $G_{i2}$ or $G_{i3}$, since co-injection of cRNA for fMLF-R along with these alpha subunits did not induce a functional response (Murphy, P. M. & McDermott, D. (1991) *J Biol. Chem.* 266, 12560–12567). In independent studies, the co-factor has been shown to be encoded by an approximately 3–3.5 kilobase transcript (Murphy, P. M. & McDermott, D. (1991) *J Biol. Chem.* 266, 12560–12567; Schultz, P., Stannek, P., Voigt, M., Jakobs, K. H., & Gierschik, P. (1992) *Biochem. J.* 284, 207–212). A recent report demonstrated that Ga-16 complements the signal transduction cascade of both C5a-R and fMLF-R, and it may be the complementing cofactor present in HL-60 and U937 (Schultz, P., et al (1992) *Biochem. J.* 284, 207–212). Xenopus oocytes were used to functionally characterize C3a Receptor. A C3a carboxy-terminal analog synthetic peptide, [WWGKKYRASKLGLAR (SEQ ID NO:3)] and to a lesser extent rC5a, but not platelet activating factor or the chemotactic peptide fMLF, elicited an electrophysiological response in oocytes injected with cRNA for C3a Receptor (FIG. 3A). Like the C5a-R and the fMLF-R, the response was dependent on the co-injection of a cofactor present in total HL-60 or U937 RNA. The exact nature of the co-factor is not known, however as the response to the C3a peptide of oocytes co-injected with C3a Receptor and U937 RNA was abolished by pertussis toxin (data not shown), it does not appear to be Gα-16, which lacks a pertussis toxin ADP-ribosylation site (Amatruda, T. T., et al (1991) Proc. Natl. Acad. Sci. USA 88:5587–5591). C3a Receptor cRNA or U937 RNA when injected alone did not elicit any response to the C3a synthetic peptide or rC5a (FIG. 3A). In a similar fashion, rC5a induced rapid activation of chloride currents in C5a-R cRNA plus U937 RNA co-injected oocytes. In addition, there was a smaller response to C3a. (FIG. 3B). Both the C5a-R as well as C3a Receptor elicited in oocytes a promiscuous response to the two anaphylatoxins. The responses detected with the C3a synthetic peptide were not an artifact of using the analogue peptide, as the native ligand elicited similar responses in oocytes injected with either receptor (data not shown).

Example 4

Stable expression in RBL-2H3 cells

To prepare C3a Receptor for expression in mammalian cells, a 1.6 kb cDNA fragment was obtained by PCR amplification that encompassed the entire C3a Receptor open reading frame. This fragment was subcloned into KpnI/Hind III sites of the mammalian expression vector, pCDN (Aiyar, N., et al (1994) *Mol. Cell. Bio.* 131, 75–86). Oligonucleotide primers used for PCR amplification were 5'-GAAGT GGT ACC ATG GCG TC-3' (SEQ ID NO:4) and 5'-GC TCC AAG CTT TCA CAC AGT TG-3' (SEQ ID NO:5) (the translation start and stop codons are underlined). RBL-2H3 cells were electroporated with either C3a Receptor or C5a-R in the pCDN mamalian expression vector (Aiyar, N., et al (1994) *Mol. Cell. Bio.* 131, 75–86), exactly as described (DeMartino, J. A., et al (1994) *J. Biol Chem.* 269, 14446–14450). Individual G418 resistant (400 µg/ml) colonies were isolated and expanded. Clonal cell lines expressing either C3a Receptor or C5a-R were chosen for further functional and binding studies.

Figure 4A:
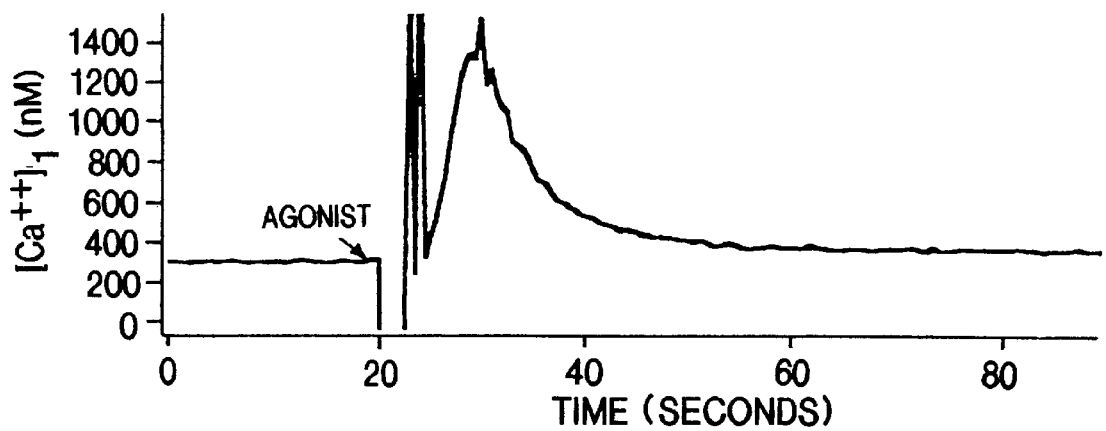
FIGS. 4 (A–B) shows oocytes expressing C3a Receptor or C5a receptor respond to both C3a and C5a. (A) Electrophysiological response of Xenopus oocytes injected with cRNA for C3a Receptor (10 ng), total U937 RNA (25 ng), or a mixture of C3a Receptor (10 ng) and U937 RNA (25 ng) to 10 nM rC5a, 10 nM C3a analogue peptide, 10 nM platelet activating factor (PAF), 10 nM fMetLeuPhe. Inset, represents typical response of oocytes co-injected with C3a Receptor cRNA+U937 RNA to 10 nM C3a. (B) Electrophysiological response of oocytes injected with C5a-R cRNA (10 ng), U937 RNA (25 ng) or a mixture of C5a-R and U937 RNA, to 10 nM rC5a or 10 nM C3a analogue peptide.
Figure 4B:
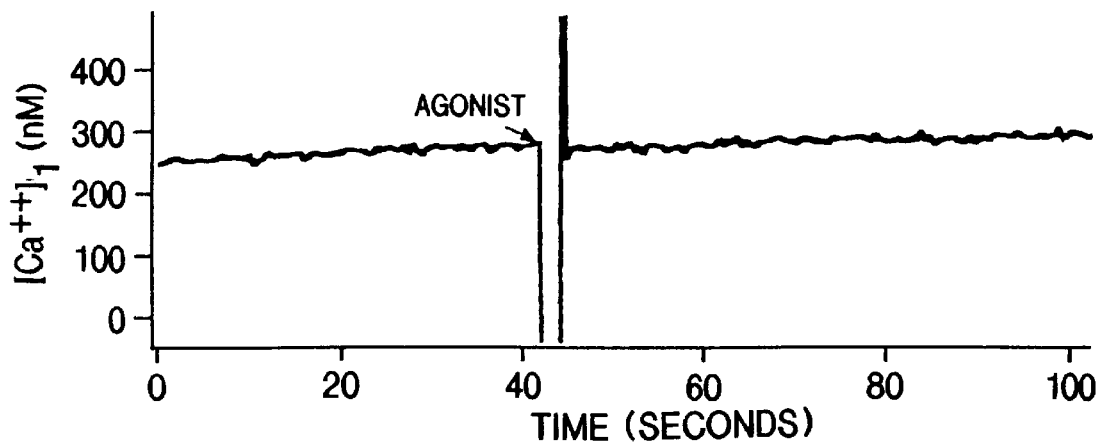
Figure 4C:
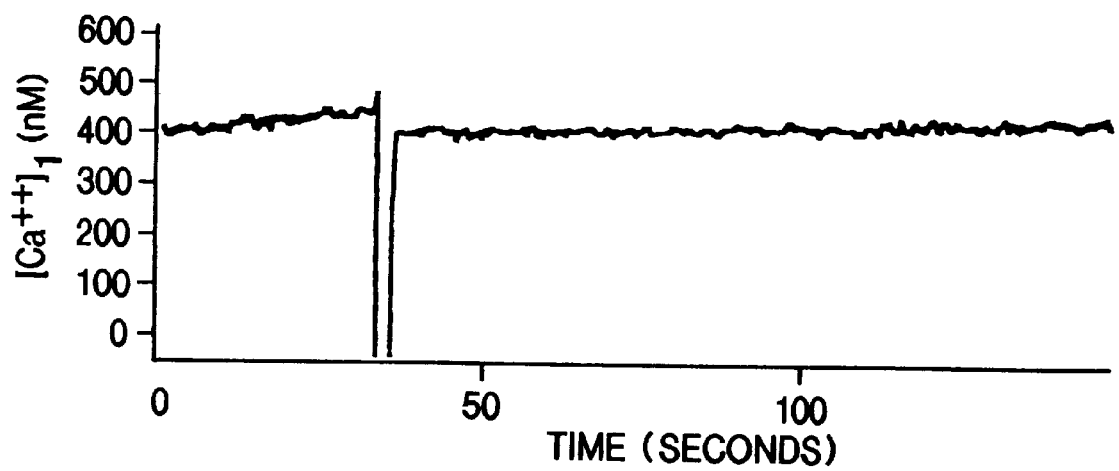
Figure 4D:
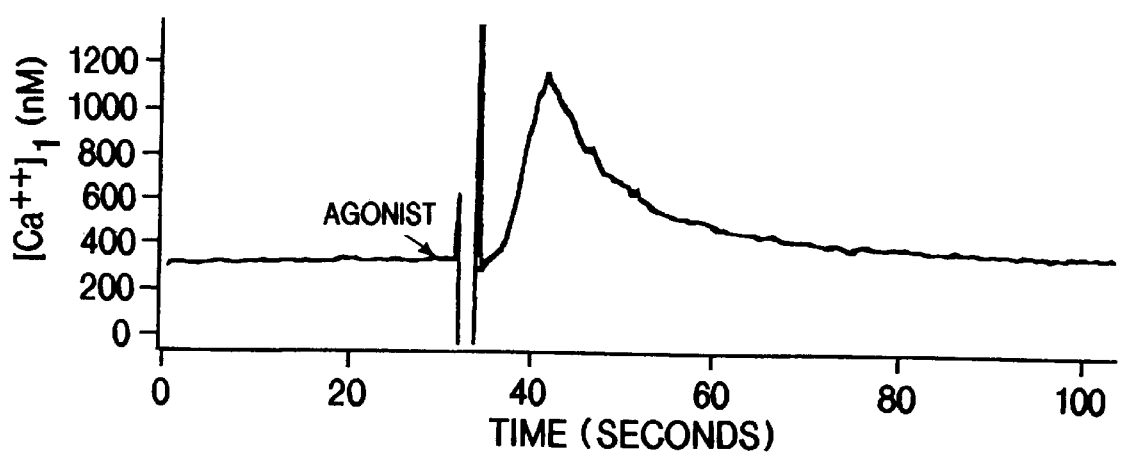

RBL-2H3 cells (Siraganian, R. P., et al (1982) *Fed. Proc.* 41, 30–34), a rat basophil cell line, when transfected with an expression plasmid encoding the C5a-R express receptors that are functionally active (DeMartino, J. A., et al (1994) *J. Biol. Chem.* 269, 14446–14450). RBL-2H3 cells were stably transfected with mammalian expression plasmids encoding the C5a-R or C3a Receptor and Fura 2 loaded cells were tested for a C5a or C3a induced mobilization of intracellular $Ca^{2+}$. C5a-R but not C3a Receptor expressing cells responded to rC5a (FIGS. 4A & B). A robust response to the C3a synthetic peptide ($EC_{50}$=3.9 nM) was detected in cells expressing C3a Receptor but no response was obtained for C5a-R expressing cells (FIGS. 4D & 4C, respectively). Similarly, C3a Receptor but not C5a-R expressing RBL-2H3 cells also responded to native human C3a ($EC_{50}$=0.3 nM, data not shown).

Figure 5:
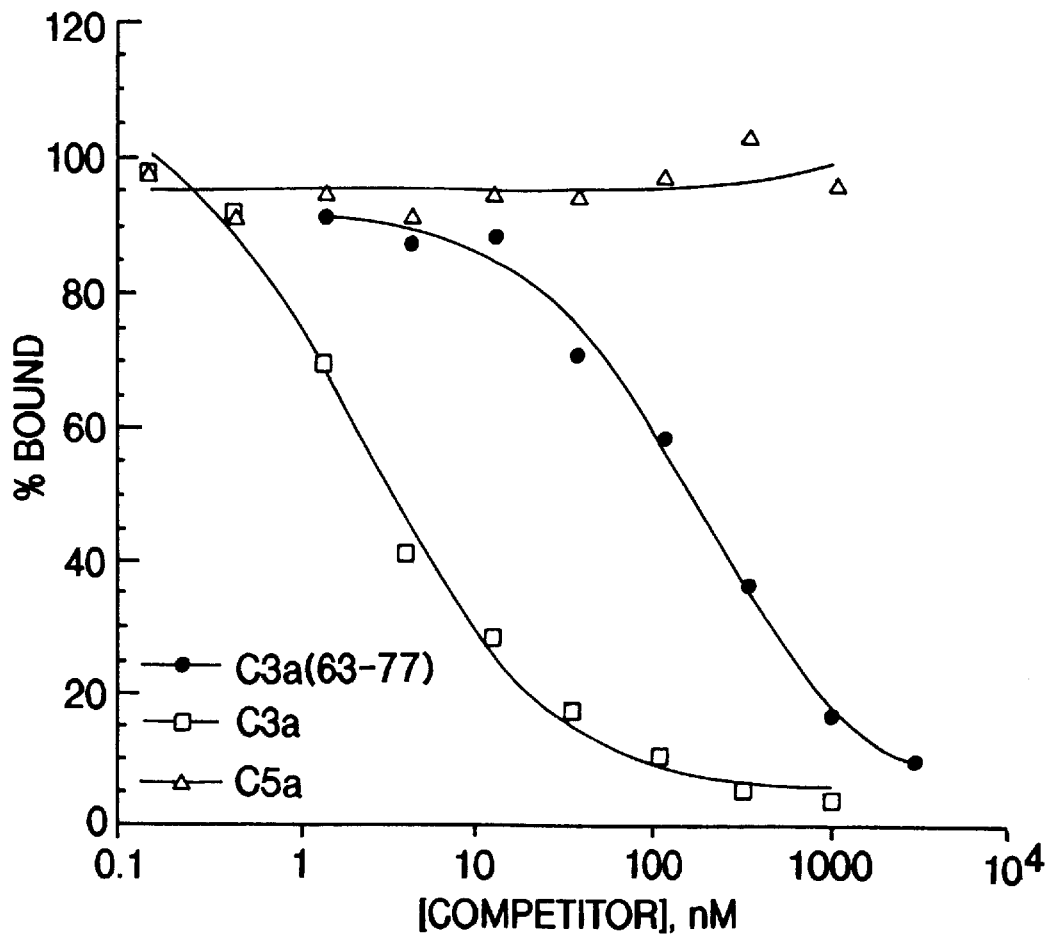
FIG. 5 shows competition of $^{125}$I-C3a binding to C3a Receptor expressing RBL-2H3 cells by increasing concentrations of C3a analogue synthetic peptide (open square), C3a (closed circle) or rC5a (open triangle).

FIG. 5 Calcium mobilization

Fura 2 loaded clonal cell lines expressing C5a-R or C3a Receptor were assayed for functional response, $Ca^{2+}$ mobilization, as described (Saussy, D. L. Jr., et al (1989) *J. Biol. Chem.* 264, 19845–19855).

FIG. 6 Binding Assay

The C3a carboxy-terminal analogue synthetic peptide, [WWGKKYRASKLGLAR (SEQ ID NO:3)] was obtained from Bachem Bioscience, Inc., King of Prussia, Pa. C3a was purchased from Advanced Research Technologies, San Diego, Calif. Human rC5a was expressed in *E. coli* and purified to homogeneity. Other agonists were obtained from Sigma, St. Louis, MO. C3a was radioiodinated using IODO-BEADS (Pierce, Rockford Ill.) to a specific activity of 100 Cilmmol. Increasing concentrations of cold competitor were added to $1\times10^6$ cells in the presence of $^{125}$-C3a (2.3 nM), and the assay was performed essentially as described (Klos, A., et al (1992) *Biochemistry* 31, 11274–11282).

C3a was radioiodinated and used in whole cell binding assays to further characterize C3a Receptor. Binding of $^{125}$-C3a to C3a Receptor expressing RBL-2H3 cells was competed by increasing concentrations of C3a ($IC_{50}$=3.0 nM) and the C3a analogue synthetic peptide ($IC_{50}$=155 nM) but not by rC5a (FIG. 5). By saturation binding and Scatchard analysis a single class of C3a binding sites was identified with an estimated Kd of 0.3 nM, and a Bmax of 32,000 receptors per cell (data not shown). Curiously, HEK 293 cells stably expressing C3a Receptor mRNA by Northern Blot, neither bound nor responded to C3a (data not shown).

It will be clear that the invention may be practiced otherwise than as particularly described in the foregoing description and examples.

Numerous modifications and variations of the present invention are possible in light of the above teachings and, therefore, are within the scope of the appended claims.

What is claimed is:

1. A method for identifying compounds which inhibit the interaction of a C3a with a C3a receptor comprising a polypeptide with amino acids 1 to 482 of SEQ ID NO:2, comprising:

contacting a cell expressing on the surface thereof a C3a receptor, said receptor being associated with a second component capable of providing a detectable signal in response to the binding of a compound to said receptor, with a compound to be screened under conditions to permit binding to the receptor; and determining whether the compound inhibits the interaction of C3a and C3a Receptor by detecting the presence or absence of a signal generated from the interaction of the C3a with C3a receptor.

2. A method for identifying inhibitor of a polypeptide comprising a polypeptide with amino acids 1 to 482 of SEQ ID NO: 2 which comprises:

determining the inhibition of binding of labeled C3a ligand to cells which have the polypeptide on the surface thereof, or to a cell membrane having the polypeptide, in the presence of a candidate compound under conditions to permit binding to the polypeptide, and determining the amount of ligand bound to the polypeptide, such that a compound capable of causing reduction of binding of the ligand is an inhibitor.

3. A method for identifying inhibitor of a C3a receptor comprising a polypeptide with amino acids 1 to 482 of SEQ ID NO: 2 which comprises:

contacting a cell expressing on the surface thereof a C3a receptor, said receptor being associated with a second component capable of providing a detectable signal in response to the binding of a compound to said receptor, with a compound to be screened under conditions to permit binding to the receptor; and determining whether the compound inhibits the interaction of C3a and C3a Receptor by detecting the presence or absence of a signal generated from the interaction of the C3a with C3a receptor.

4. A method for identifying inhibitor of a polypeptide comprising a polypeptide with an amino acid sequence of SEQ ID NO: 2, in which one to ten amino acid residues are substituted, deleted or added, comprising:

determining the inhibition of binding of labeled C3a ligand to cells which have the polypeptide on the surface thereof, or to a cell membrane having the polypeptide, in the presence of a candidate compound under conditions to permit binding to the polypeptide, and determining the amount of ligand bound to the polypeptide, such that a compound capable of causing reduction of binding of the ligand is an inhibitor.

5. A method of claims 1, 2, 3, or 4 in which cell is selected from the group consisting of HEK 293, CHO, yeast, RBL-2H3 and Xenopus oocytes.

6. A method of claim 1 or 3 in which signal detected is selected from the group consisting of calcium ions, hydrogen ions, phospholipase C, and phospholipase D.

7. A method of claim 1 or 3 which uses FLPR.

8. A method of claim 2 or 4 in which C3a is labeled with I-125.

* * * * *